United States Patent
Zalipsky et al.

(10) Patent No.: US 6,365,179 B1
(45) Date of Patent: Apr. 2, 2002

(54) CONJUGATE HAVING A CLEAVABLE LINKAGE FOR USE IN A LIPOSOME

(75) Inventors: Samuel Zalipsky, Redwood City, CA (US); Alberto A. Gabizon, Jerusalem (IL)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/556,610

(22) Filed: Apr. 21, 2000

Related U.S. Application Data

(60) Provisional application No. 60/130,897, filed on Apr. 23, 1999.

(51) Int. Cl.$^7$ .................. A61K 9/127; A61K 38/00; C08B 11/00; A01N 61/00
(52) U.S. Cl. ............... 424/450; 424/85.1; 205/254; 530/336; 536/84; 514/1
(58) Field of Search ............... 424/85.1, 450; 205/254; 530/336; 536/84; 514/1

(56) References Cited

U.S. PATENT DOCUMENTS 5,891,468 A   4/1999   Sequus .................. 424/450

OTHER PUBLICATIONS

Dmitri Kirpotin, "Liposomes with detachable polymer coating: destabilization . . . ," FEBS Letters, vol. 388 (No. 2–3), p. 115–118, (May 16, 1996).

Markus Johnsson et al., "Optimization of Drug Loading Procedures . . . ," Journal of Liposome Res., vol. 9 (No. 1), p. 53–79, (Feb. 16, 1999).

Samuel Zalipsky, "New detachable poly(ethylene glycol) conjugates . . . ," Bioconjugate Chemistry, vol. 10 (No. 5), p. 703–707, (Sep. 20, 1999).

Christa E. Mueller et al., "Amphiphilic Unsymmetrical Disulfides . . . (Untranslated)," Archiv der Pharmazie, vol. 322 (No. 6), p. 343–350, (May 16, 1989).

Mohamed Gaber et al., "Thermosensitive sterically stabilized liposomes.," Pharmaceutical Res., vol. 12 (No. 10), p. 1407–1416, (May 16, 1995).

Jan Vaage et al., "Therapy of human ovarian carcinoma xenograpfts . . . ," Cancer, vol. 72 (No. 12), p. 3671–3675, (May 16, 1993).

Therapy of a Xenografted Human Colonic Carcinoma . . . , "International Journal of Cancer," vol. 80 (No. 1), p. 134–137, (Jan. 5, 1999).

J. Vaage et al., "Tissue Distribution and Therapeutic Effect of Intravenous . . . ," Cancer, vol. 73 (No. 5), p. 1478–1484, (May 16, 1994).

J. Vaage et al., "Therapy of Primary and metastatic Mouse Mammary . . . ," International Journal of Cancer, vol. 51 (No. 6), p. 942–948, (1992).

Sadao Hirota, "Physicochemical specification of drug carrying . . . ," International Jrl. of Pharmaceutics, vol. 162 (No. 1–2), p. 185–194, (Mar. 20, 1998).

*Primary Examiner*—Jezia Riley
(74) *Attorney, Agent, or Firm*—Paul B. Simboli; Judy M. Mohr

(57) ABSTRACT

Conjugates of a hydrophobic moiety, such as a lipid, linked through a cleavable dithiobenzyl linkage to a therapeutic agent are described. The dithiobenzyl linkage is susceptible to cleavage by mild thiolysis, resulting in release of the therapeutic agent in its original form. The linkage is stable under nonreducing conditions. The conjugate can be incorporated into liposomes for administration in vivo and release of the therapeutic agent in response to endogeneous in vivo reducing conditions or in response to administration of an exogeneous reducing agent.

42 Claims, 18 Drawing Sheets

CONJUGATE HAVING A CLEAVABLE LINKAGE FOR USE IN A LIPOSOME

This application claims the benefit of U.S. Provisional Application No. 60/130,897, filed Apr. 23, 1999, incorporated herein by reference in its entirety now abandoned.

FIELD OF THE INVENTION

The present invention relates to a conjugate comprised of a hydrophobic moiety, a cleavable linkage, and a therapeutic agent. More particularly, the present invention relates to conjugates comprised of a lipid, a cleavable linkage and a drug incorporated into a liposomal formulation. The conjugates are cleavable under mild thiolytic conditions in vivo for release of the drug in an unmodified state.

BACKGROUND OF THE INVENTION

Liposomes are closed lipid vesicles used for a variety of therapeutic purposes, and in particular, for carrying therapeutic agents to a target region or cell by systemic administration of liposomes. Liposomes having a surface grafted with chains of water-soluble, biocompatible polymer, in particular polyethylene glycol, have become important drug carries. These liposomes offer an extended blood circulation lifetime over liposomes lacking the polymer coating. The grafted polymer chains shield or mask the liposome, thus minimizing nonspecific interaction by plasma proteins. This in turn slows the rate at which the liposomes are cleared or eliminated in vivo since the Liposome circulate unrecognized by macrophages and other cells of the reticuloendothelial system. Furthermore, due to the so-called enhanced permeability and retention effect, the liposomes tend to accumulate in sites of damaged or expanded vasculature, e.g., tumors, sites of inflammation.

An extended blood circulation time is often desired to allow systemically administered liposomes to reach a target region, cell or site. For example, a blood circulation lifetime of greater than about 12 hours is preferred for liposomal-therapy to a tumor region, as the liposomes must systemically distribute and then extravasate into the tumor region.

One problem associated with liposome-based therapy is retention of drug within the Liposome for a time sufficient for systemic distribution. This problem is of particular concern when long-circulating liposomes, i.e., liposomes with grafted polymer chains, are administered. Relatively few drugs can be efficiently loaded and retained for a long duration and subsequently released.

One approach to improving drug retention is to select lipid bilayer components that render the bilayer less permeable to entrapped drug. However, the lipid bilayer should be sufficiently fluidic such that the drug is released, for example by transport across the lipid bilayer or by lipid vesicle breakdown, at the desired time, e.g., after localization at a target site or sufficient biodistribution.

Another approach to improving drug retention is to covalently attach the drug to a lipid in the liposomal lipid bilayer (Waalkes, et al., *Selective Cancer Therap.*, 6:15–22 (1990); Asai, et al., *Biol. Pharm. Bull.*, 21:766–771 (1998)).

It would be desirable to formulate a liposome composition having a long blood circulation lifetime and capable of retaining an entrapped drug for a desired time, yet able to release the drug on demand. One approach described in the art for achieving these features has been to formulate a liposome from a non-vesicle-forming lipid, such as dioleoylphosphatidylethanolamine (DOPE), and a lipid bilayer stabilizing lipid, such as methoxy-polyethylene glycol-distearoyl phosphatidylethanoLamine (mPEG-DSPE) (Kirpotin, D, et al., *FEBS Lett.* 388:115–118 (1996)). In this approach, the mPEG is attached to the DSPE via a cleavable linkage. Cleavage of the linkage destabilizes the liposome for a quick release of the liposome contents.

Labile bonds for linking PEG polymer chains to liposomes has been described (U.S. Pat. Nos. 5,013,556, 5,891,468; WO 98/16201). The labile bond in these liposome compositions releases the PEG polymer chains from the liposomes, for example, to expose a surface attached targeting ligand or to trigger fusion of the liposome with a target cell.

To date, however, a means of releasing polymer chains from liposomes under conditions suitable for in vivo use has not been achieved. For example, some releasable linkages require a potent thiolytic agent, such as 1,4-dithiothreitol, to achieve release of the polymer chains. This reducing agent is unacceptable for in vivo use. Another problem with known releasable linkages joining PEG to a liposome lipid is that cleavage of the releasable bond generates an unnatural and undesirable modified lipid. Accordingly, there remains a need in the art for a cleavable linkage that is suitable for in vivo use and which, after cleavage, yields the drug or therapeutic agent in its natural, unmodified form.

In EP 0317957, Senter describes a drug-antibody prodrug, where the antibody is linked to a drug using a disulfide benzyl carbamate or carbonate linker, and reduction of the disulfide bond effects release of the drug. Senter's teaching is specific to cleavage of a drug-ligand prodrug molecule, under the action of reducing agents such as 1,4-dithiothreitol, glutathione, NADH and NADPH. The behavior of such a linker, when incorporated into a liposome that circulates through the bloodstream, cannot be predicted based on the Senter disclosure. For example, in liposomes, the linker between the polymer and the lipid would be buried or masked in the PEG coating. It is relatively easy to envision release of a single drug-ligand prodrug as in Senter; however, release of the linker when a part of a densely packed barrier as in a liposome surface coating of polymer chains is less predictable.

As noted above, an extended blood circulation time is a desirable feature of PEG-coated liposomes, with blood circulation lifetimes of greater than about 12 hours being preferred for liposomal-therapy to a tumor region. The disclosure of Senter provides no guidance as to the release kinetics of a conjugate incorporated into a liposome under endogenous reducing conditions, such as during blood circulation of the liposome.

SUMMARY OF THE INVENTION

Accordingly, it is an object of the invention to provide a liposome composition wherein the drug is retained for a desired period of time for release from the liposome.

It is another object of the invention to provide a conjugate for use in a liposome, wherein the conjugate is comprised of a hydrophobic moiety for anchoring into the lipid bilayer, a linkage cleavable n response to mild thiolytic conditions and a therapeutic agent.

In one aspect, the invention includes a conjugate for use in a liposomal drug-delivery vehicle, the conjugate having the general structural formula:

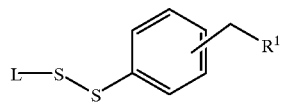

wherein L is a hydrophobic moiety suitable for incorporation into a liposomal lipid bilayer, $R^1$ represents a therapeutic drug covalently attached to the dithiobenzyl moiety, and where orientation of the $CH_2R^1$ group is selected from the ortho position and the para position.

In one embodiment, the therapeutic drug is covalently attached by a linkage selected from the group consisting of urethane, amine, amide, carbonate, thio-carbonate, ether and ester.

In another embodiment, L is selected from the group consisting of cholesterol, a diacylglycerol, a phospholipid and derivatives thereof.

In yet another embodiment, L is a diacylglycerol derivative to yield a conjugate having the general structural formula:

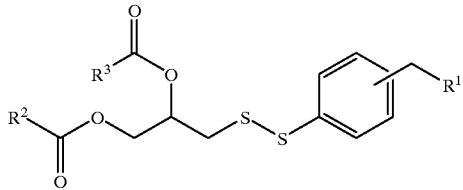

wherein $R^2$ and $R^3$ are hydrocarbons having between about 8 to about 24 carbon atoms, or in another embodiment, from about 12 to about 22 carbon atoms. In still another embodiment, $R^2$ and $R^3$ are hydrocarbon chains of the same length.

In another embodiment, the drug is selected from the group consisting of mitomycin C, mitomycin A, bleomycin, doxorubicin, daunorubicin, fluorodeoxyuridine, iododeoxyuridine, etoposide, AZT, acyclovir, vidarabine, arabinosyl cytosine, pentostatin, quinidine, atropine, chlorambucil, methotrexate, mitoxantrone and 5-fluorouracil.

In still another embodiment, the therapeutic drug is covalently linked to the dithiobenzyl moiety to form a conjugate having the structure:

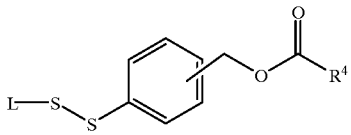

wherein $R^4$ represents a residue of the therapeutic drug.

$R^4$ in one embodiment is a therapeutic drug residue containing a primary or a secondary amine moiety thereby forming a urethane linkage be-ween the dithiobenzyl and the therapeutic drug. In this embodiment, the therapeutic drug can be, for example, mitomycin A, mitomycin C, bleomycin or a polypeptide.

In another embodiment, $R^4$ is a residue of a carboxyl-containing therapeutic drug, which forms an ester linkage between the dithiobenzyl and the therapeutic drug. Exemplary drugs in this embodiment include chlorambucil or methotrexate.

In another embodiment, $R^4$ is a therapeutic drug residue containing a hydroxyl moiety thereby to form a carbonate linkage between the dithiobenzyl and the therapeutic drug. Exemplary drugs in this embodiment include fluorodeoxyuridine, iododeoxyuridine, etoposide, AZT, acyclovir, vidarabine, arabinosyl cytosine, pentostatin, quinidine, mitoxantrone and atropine.

In another aspect, the invention includes a liposome composition, comprising liposomes composed of vesicle-forming lipids including from about 1 to about 30 mole percent of a conjugate having the general structural described above. The therapeutic drug is released from the conjugate in vivo in response to a physiologic condition or an artificially induced condition.

In yet another aspect, the invention includes a method for retaining a drug in a liposome, comprising preparing liposomes comprised of a vesicle-forming lipid and of between about 1 to about 30 mole percent of a conjugate described above. The liposomes effectively retain the drug in the liposomes until release from the conjugate in response to a physiologic condition or an artificially induced condition.

These and other objects and features of the invention will be more fully appreciated when the following detailed description of the invention is read in conjunction with the accompanying drawings.

DETAILED DESCRIPTION OF THE INVENTION

I. Definitions

Figure 1:
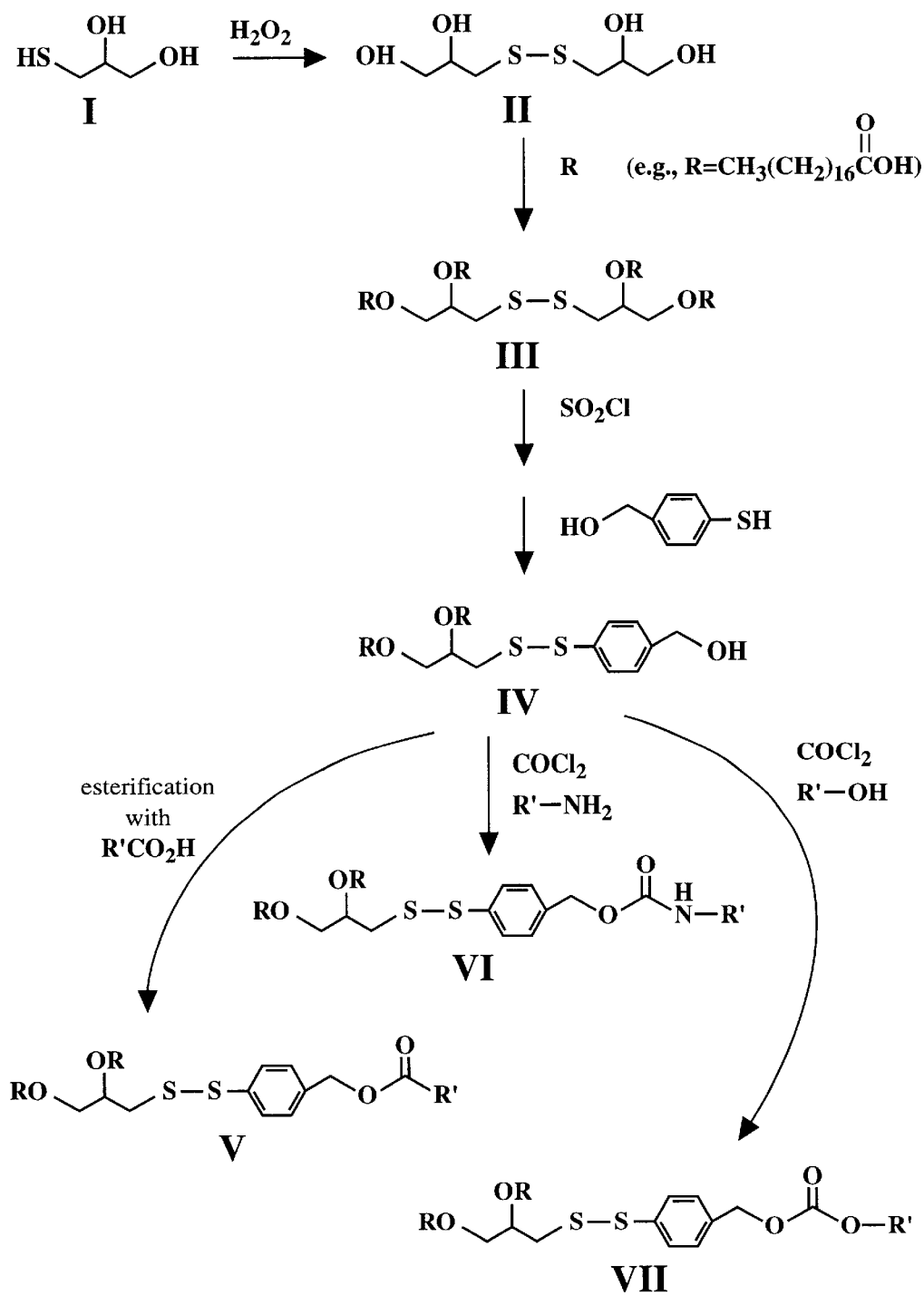
FIG. 1 shows a synthetic reaction scheme for preparation of para-diacyldiglycerol-dithiobenzylalcohol for further reaction with amine-, hydroxy- or carboxyl-containing drugs.

The phrase "hydrophobic moiety suitable for incorporation into a liposomal lipid bilayer" intends any material comprising a hydrophobic portion capable of being integrated with the hydrophobic bilayer region of a liposomal lipid bilayer. Such hydrophobic moieties are typically lipids, including amphipathic lipids having a hydrophobic lipid tail and a hydrophilic polar head, such as phospholipids and diacylglycerols. Triglycerides, sterols, derivatives of phospholipids, diacylglyerols, sterols and triglycerides and other lipids derived from a natural source or synthetically prepared are also contemplated.

The term "residue" as in "therapeutic drug residue" intends a drug molecule that has been reacted to form an linkage with another molecule where at least one atom of the drug molecule is replaced or has been sacrificed to from the linkage.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like.

The following abbreviations are used herein: PEG, poly (ethylene glycol); mPEG, methoxy-PEG; DTB, dithiobenzyl; DSPE, distearoyl phosphatidyl(ethanolamine; HSPC, hydrogenated soy phosphatidylcholine; MMC, mitomycin C.

II. Conjugate Composition and Method of Preparation

In one aspect, the invention includes a conjugate of the form:

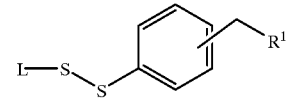

wherein L is a hydrophobic moiety suitable for incorporation into a liposomal lipid bilayer, $R^1$ represents a therapeutic drug residue covalently attached to the dithiobenzyl moiety, and where orientation of the $CH_2R^1$ group is selected from the ortho position and the para position. The hydrophobic moiety, L, is typically a lipid such as a diacylglycerol, a sterol, a phospholipid, derivatives of these lipids, other naturally-occurring lipids and their synthetic analogs.

In the conjugate, a therapeutic drug is attached to the dithiobenzyl moiety by a covalent linkage, thereby forming a drug residue, represented by $R^1$ in the structure. The linkage will vary according to the drug and the reaction chemistry, as will be appreciated by those of skill in the art. In preferred embodiments, the therapeutic drug is covalently attached to the diithiobenzyl moiety by a linkage selected from the group consisting of urethane, amine, amide, carbonate, thio-carbonate, ether and ester.

A urethane linkage takes the form of O(C=O)NH—R⁴ or O(C=O)N=R⁴, where R⁴ represents the therapeutic drug residue. For example, a drug containing a primary or secondary amine, such as mitomycin C, mitomycin A, bleomycin and therapeutic polypeptides to name a few, is reacted to from a urethane linkage with the amine moiety in the drug.

A carbonate linkage takes the form of O(C=O)O—R⁴, where R⁴ represents the drug residue and the carbonate linkage derives from a phenol or alcohol or hydroxyl moiety in the drug. A thio-carbonate takes the form of O(C=O)S—R⁴, where R⁴ represents the drug residue and the linkage derives from a moiety in the drug. Exemplary drugs having such a moiety for reaction with dithiobenzyl alcohol to form a carbonate linkage include fluorodeoxyuridine, iododeoxyuridine, etoposide, AZT, acyclovir, vidarabine, arabinosyl cytosine, pentostatin, quinidine, mitoxantrone and atropine.

An ester linkage takes the form of O(C=O)—R⁴, where R⁴ represents the drug residue. The linkage derives from reaction with a carboxylic acid moiety in the therapeutic drug, and an example of a conjugate having an ester linkage between chlorambucil and dithiobenzyl is described below. Methotrexate is another example of a drug capable of forming an ester linkage with the dithiobenzyl moiety of the conjugate.

Conjugates having a urethane, carbonate or ester linkage attaching the drug to the dithiobenzyl moiety can generally be represented by the following structure:

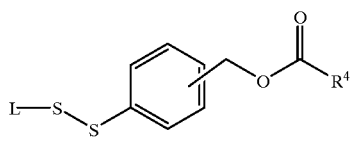

wherein R⁴ represents a residue of the therapeutic drug.

In another embodiment, the conjugate includes an ether linkage, which takes the form of O—R⁴, where R⁴ represents the therapeutic drug residue. The linkage typically derives from reaction with an alcohol functionality on the drug.

An amine linkage is of the form N=R⁴, where R⁴ represents the drug residue and the linkage is a direct attachment with the CH₂ moiety of the dithiobenzyl with a N in the drug. A conjugate with the drug 5-fluorouracil where an amine linkage is formed will be described below. An amide linkage can also be formed with a peptide as the therapeutic agent, where the free carboxyl of an amino acid residue, such as an aspartic acid or glutamic acid, is condensed with dithiobenzylamine.

An amide linkage takes the form of NH(C=O)—R⁴, where R⁴ represents the drug residue.

FIG. 1 shows a synthetic reaction scheme for preparation of exemplary conjugates in accord with the invention. In this embodiment, synthesis of an intermediate compound, para-diacyldiglyceroldithiobenzalcohol (Compound IV), is prepared for further reaction with a selected therapeutic drug. Compound IV is prepared, as described in Example 1, by reacting 3-mercapto-1,2-propanediol (Compound I) with hydrogen peroxide to form rac-3,3'-dithiobis(1,2-propanediol) (Compound II). Rac-3,3'-dithiobis(1,2-propanediol) is acylated with a hydrophobic moiety R. For example, R can be a fatty acid having from about 8 to about 24 carbon atoms. Example 1 details the reaction procedure where R is stearic acid. In another embodiment, R is a fatty acid having from about 12 to about 22 carbon atoms. Acylation of Compound II yields Rac-3,3'-dithiobis(1,2-propanedistearoyl) (Compound III), which is reacted with sulfuryl chloride and 4-mercaptobenzalcohol to form the desired intermediate product, para-diacyldiglycerol-dithiobenzalcohol (Compound IV). Compound IV is readily reacted with a drug containing a reactive carboxyl moiety (R'CO₂H) to form a lipid-dithiobenzyl (DTB)-drug conjugate where the drug is joined to the DTB via an ester linkage (Compound V). Compound IV is also readily reacted with a drug containing a reactive amine moiety (R'-NH₂) to yield a lipid-DTB-drug conjugate where the drug is joined to the DTB by a urethane linkage (Compound VI). Compound IV is also readily reacted with a drug containing a reactive hydroxyl moiety (R'OH) to form a lipid-DTB-drug conjugate where the drug is joined to the DTB by a carbonate linkage (Compound VII).

A variety of drugs are contemplated for use in the conjugate of the invention. In particular, the invention contemplates drugs having an amine (NH or NH₂), carboxyl, sulfhydryl or hydroxyl moiety suitable for reaction. As used herein, "suitable for reaction" implies that the drug has one of the recited moieties capable of reacting with the dithiobenzyl moiety, in the form of, for example, dithiobenzyl alcohol. Exemplary drugs include 5-fluorouracil, which has an NH group suitable for reaction, chlorambucil, which has a reactive carboxyl and mitomycin C, which has a reactive amine (aziridine group). These drugs are used to illustrate synthesis of exemplary embodiments of the invention and are discussed with respect to FIGS. 3–9. Other exemplary drugs contemplated for use include mitomycin C, mitomycin A, bleomycin, doxorubicin, daunorubicin, fluorodeoxyuridine, iododeoxyuridine, etoposide, AZT, acyclovir, vidarabine, arabinosyl cytosine, pentostatin, quinidine, atropine, chlorambucil, methotrexate, mitoxantrone and 5-fluorouracil It will be appreciated that polypeptides, aminoglycosides, alkaloids are all also suitable for use in the invention.

Example 1 also details the reaction conditions for preparation of ortho-diacyldiglyceroldithiobenzalcohol, which can serve as a intermediary compound to form the conjugate.

Figure 2A:
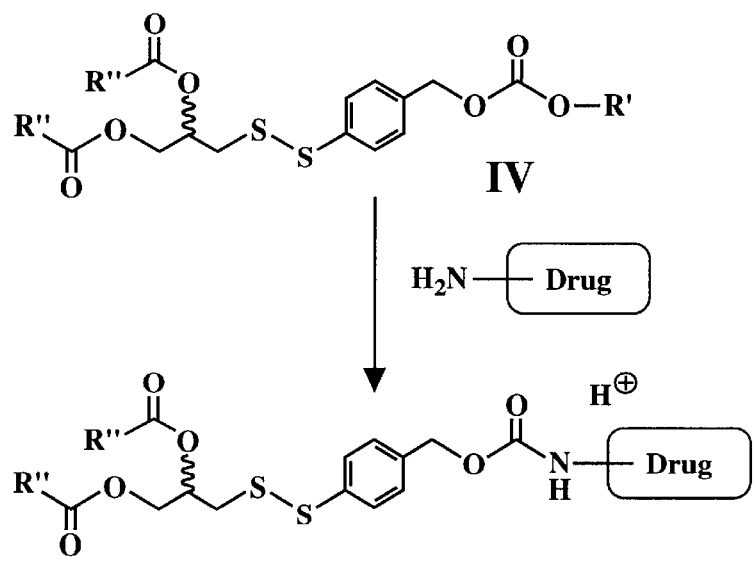
FIG. 2A shows a general reaction scheme for attachment of an amino-containing drug to a reactive diacyldiglycerol-dithiobenzylcarbonate.
Figure 2B:
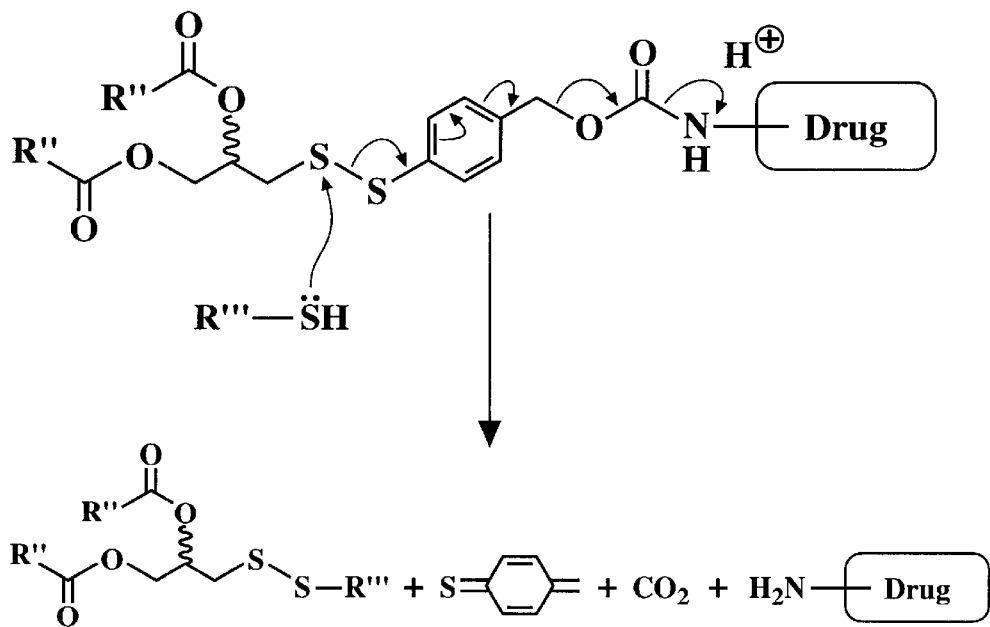
FIG. 2B shows the products after thiolytic cleavage of the conjugate in FIG. 2A.

FIGS. 2A–2B show preparation of a lipid-DTB-drug conjugate (FIG. 2A), and thiolytic cleavage of the conjugate in the presence of a reducing agent (FIG. 2B). As shown in FIG. 2A, Compound VII of FIG. 1 where the hydrophobic moiety R is derived from a fatty acid R" (CO)OH, such as stearic acid (CH₃(CH₂)₁₆CO₂H), is reacted with an amine-containing drug, H₂N-drug, in the presence of phosgene (COCl₂). This reaction yields the lipid-DTB-drug conjugate illustrated in FIG. 2A. The conjugate, upon exposure to reducing conditions, i.e., a reducing agent such as cysteine or glutathione, decomposes to yield the products shown in FIG. 2B. As shown, thiolytic cleavage of the conjugate results in regeneration of the drug in an unmodified, natural state. This is a desirable feature, since, as will be shown below, the drug in conjugate can be readily incorporated into liposomes for administration in vivo to a subject. Further, the drug in the form of the conjugate is not toxic, as will also be shown below. After administration and upon exposure to endogeneous reducing agents or exposure to an exogeneous reducing agent, the conjugate decomposes to yield the drug in its native state and with biological activity.

Figure 3A:
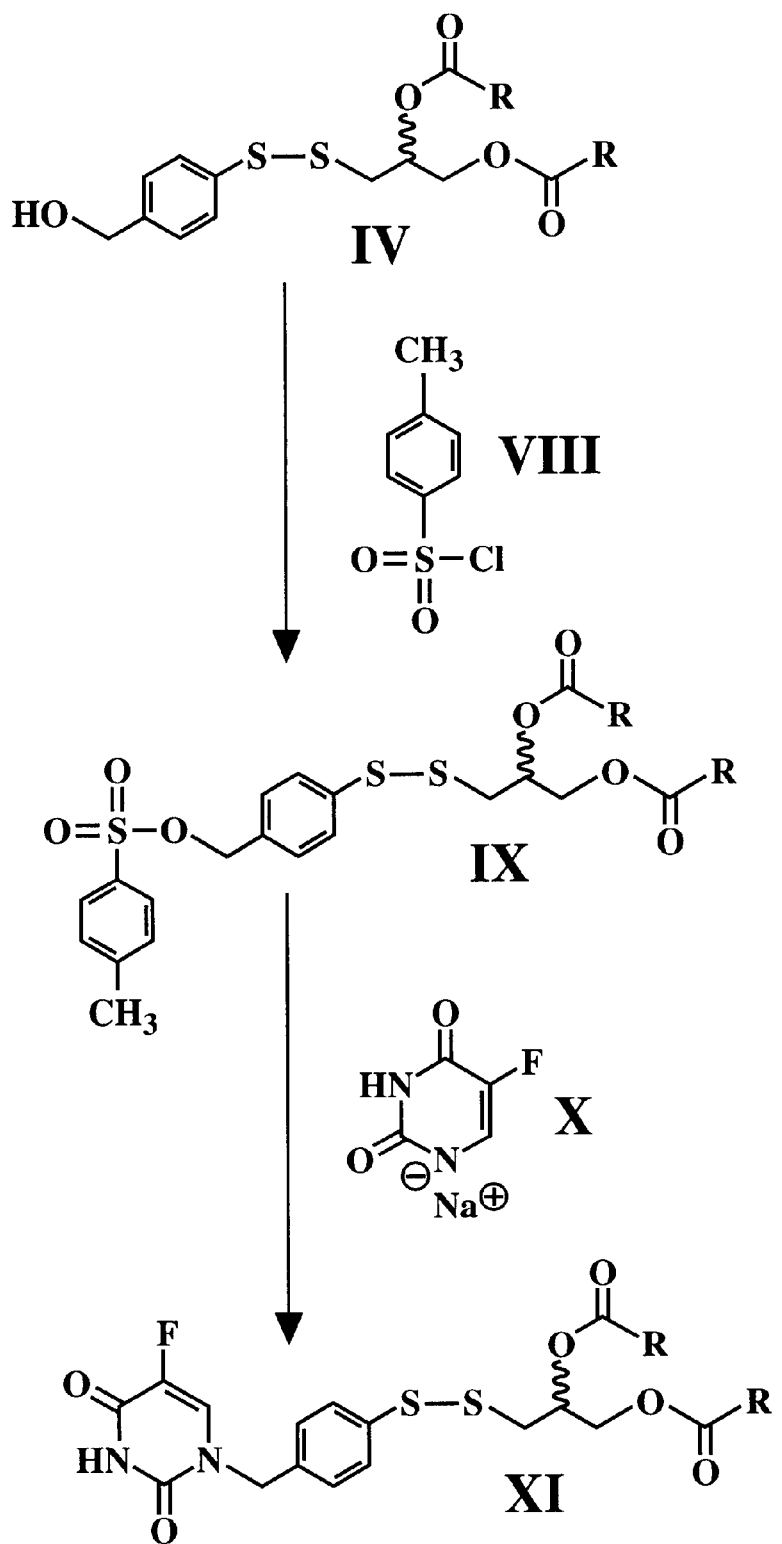
FIG. 3A shows a synthetic reaction scheme for preparation of a diacyldiglycerol-dithiobenzyl-5-fluorouracil conjugate.
Figure 3B:
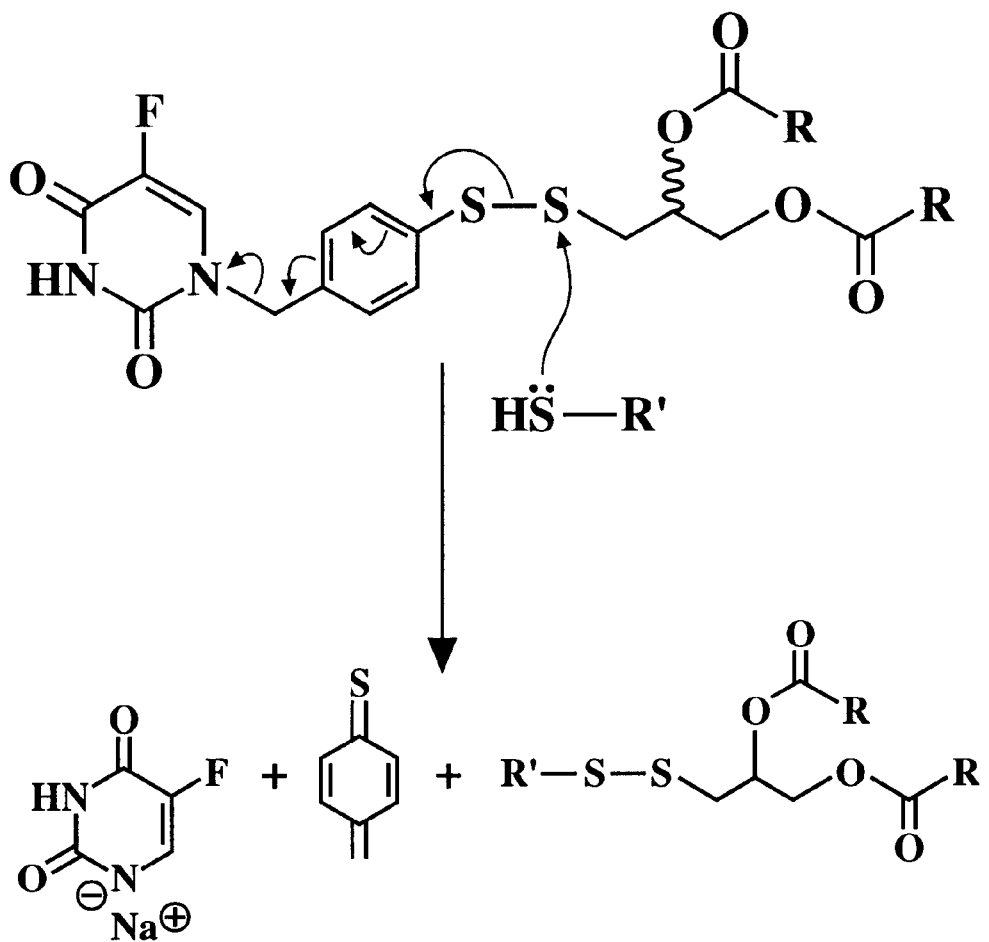
FIG. 3B shows the products after thiolytic cleavage of the conjugate in FIG. 3A.

In FIG. 3A, a synthetic reaction scheme for preparation of a conjugate of 5-fluorouracil is illustrated. Compound IV, para-diacyl-diglycerol-dithiobenzalcohol, is reacted with para-toluenesulfonyl chloride to form the intermediate compound IX. Reaction with 5-fluorouracil anion or sodium salt (Compound X) yields the desired lipid-DTB-5-fluorouracil conjugate (Compound XI). Decomposition of the lipid-DTB-5-fluorouracil conjugate (Compound XI) upon exposure to a reducing agent, R'-SH, is shown in FIG. 3B. Thiolytic cleavage of the conjugate results in regeneration of 5-fluorouracil in an unmodified form.

Figure 4:
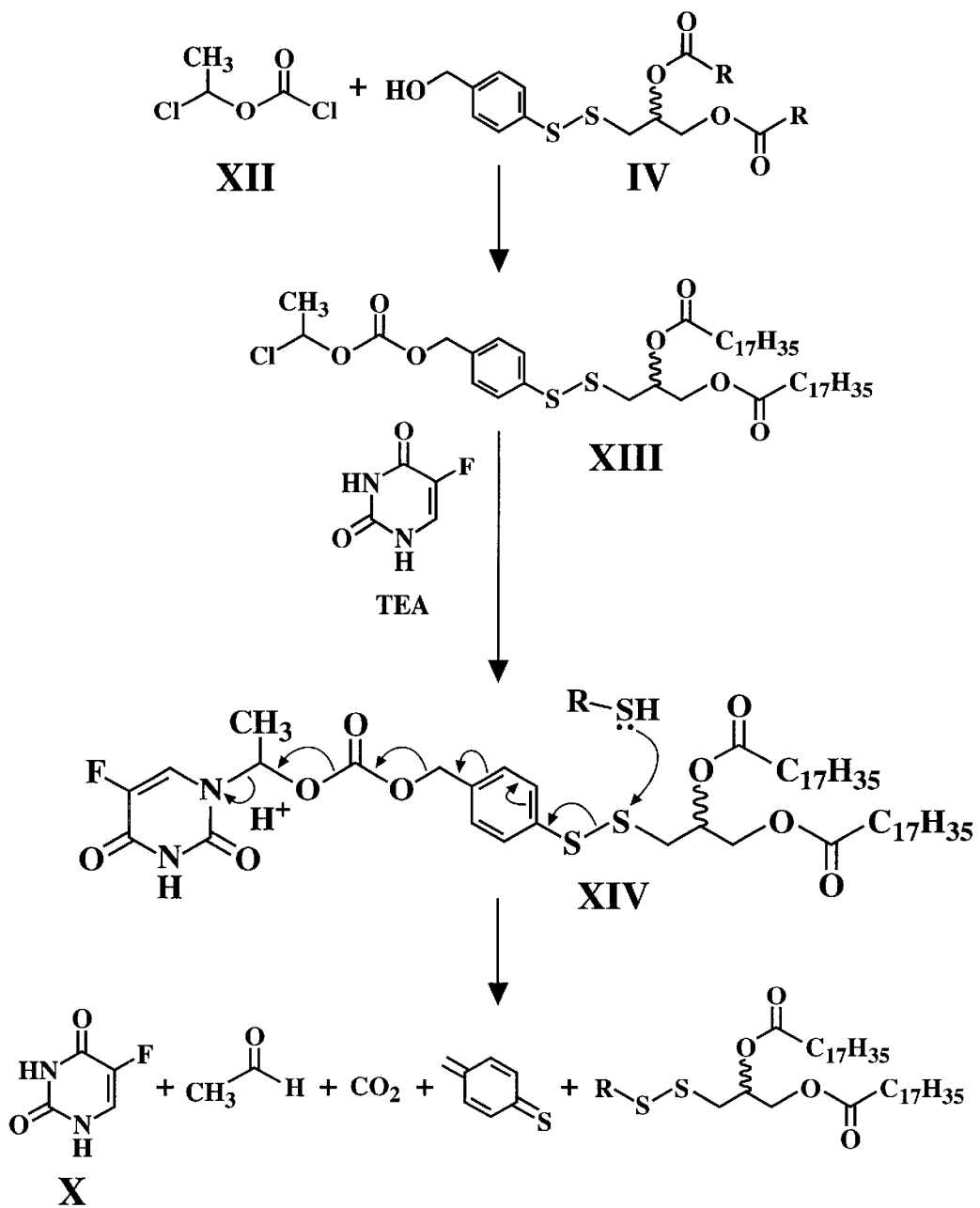
FIG. 4 shows an alternative synthetic reaction scheme for preparation of a diacyldiglycerol-dithiobenzyl-5-fluorouracil conjugate and the products after thiolytic cleavage of the conjugate.

FIG. 4 shows an alternative synthetic reaction scheme for preparation of a diacyldiglycerol-DTB-5-fluorouracil conjugate. In FIG. 4, 1-chloroethyl chloroformate (Compound XII) is reacted with para-diacyl-diglycerol-dithiobenzalalcohol (Compound IV) to form a reactive chloroethyl carbonate-DTB-diacyldiglycerol intermediate (Compound XII). The intermediate is subsequently reacted with 5-fluorouracil in the presence of triethanolamine (TEA) to yield a lipid-DTB-5-fluorouracil conjugate (Compound XIV). Thiolytic cleavage of the conjugate and regeneration of 5-fluorouracil is also shown in FIG. 4.

Figure 5:
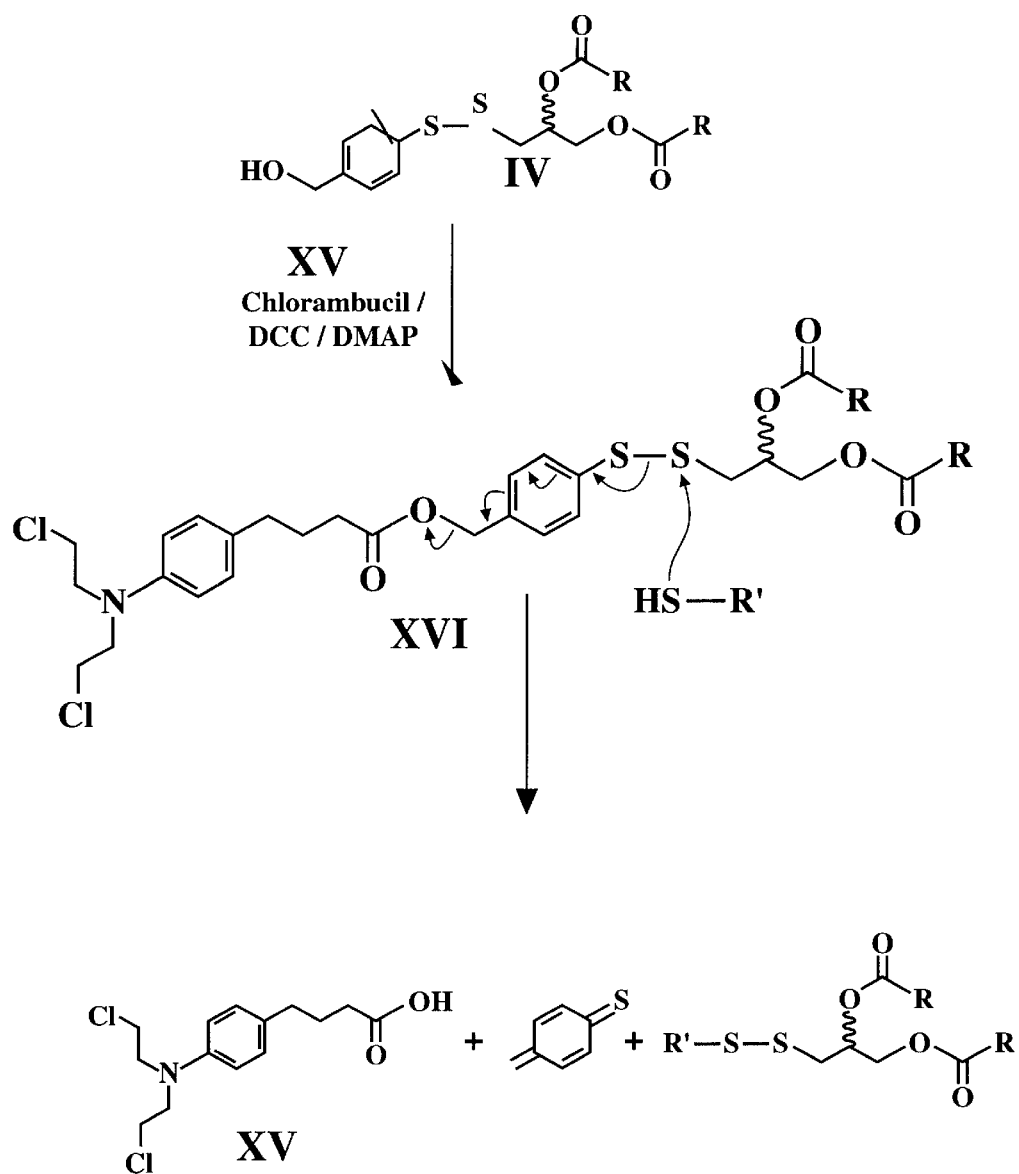
FIG. 5 shows a synthetic reaction scheme for preparation of a diacyldiglycerol-dithiobenzyl-chlorambucil conjugate and the products after thiolytic cleavage of the conjugate.

Another embodiment of the conjugate is shown in FIG. 5. In this embodiment, a drug containing a reactive carboxyl moiety, chlorambucil (Compound XV), is reacted with para-diacyl-diglycerol-dithiobenzalalcohol (Compound IV) in the presence of 1,3-dicyclohexycarbodiimide (DCC) and dimethylaminopyridine (DMAP) to form a lipid-DTB-chlorambucil conjugate (Compound XVI). Upon exposure to a reducing agent, the conjugate thiolytically decomposes to the products shown. Chlorambucil is subsequently regenerated in an unmodified state.

Figure 6A:
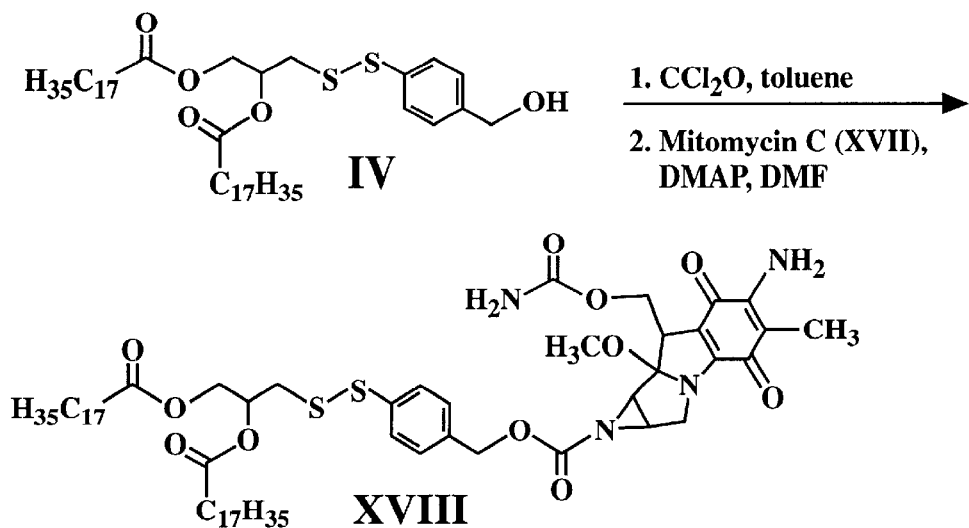
FIG. 6A shows a synthetic reaction scheme for preparation of a diacyldiglycerol-dithiobenzyl-mitomycin-C conjugate.

FIG. 6A shows the synthesis of a conjugate in accord with another embodiment of the invention. In the reaction scheme shown, mitomycin C (Compound XVII, FIG. 6B), a drug containing a reactive amine moiety, is reacted with para-diacyl-diglycerol-dithiobenzalalcohol (Compound IV) in the presence of phosgene to form a diacyldiglycerol-dithiobenzyl-mitomycin-C conjugate (Compound XVIII). Details of the synthesis are provided in Example 2.

Figure 6B:
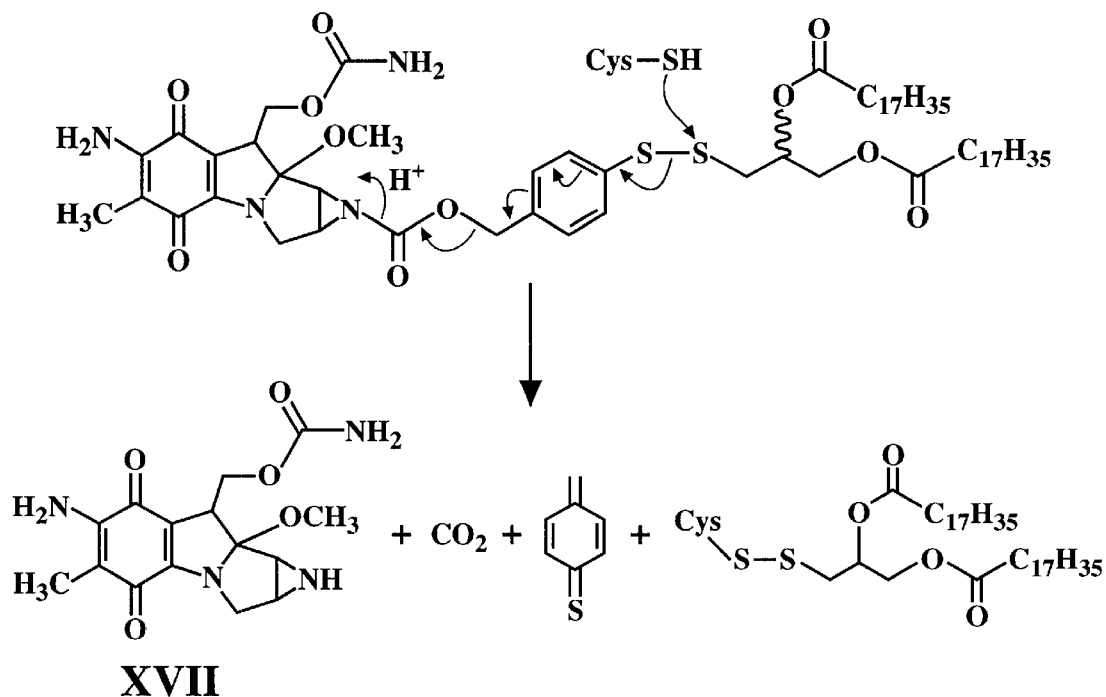
FIG. 6B shows the products after thiolytic cleavage of the conjugate in FIG. 6A.

FIG. 6B shows the thiolytic decomposition of a diacyldiglycerol-DTB-mitomycin-C conjugate. In the presence of a reducing agent, the conjugate decomposes to regenerate mitomycin C (Compound XVII) and the other products shown.

As noted above, the hydrophobic moiety in the conjugate can be selected from any number of hydrophobic moieties, e.g., lipids. In the examples above, a diacyldiglycerol lipid was used to form conjugates having the structure:

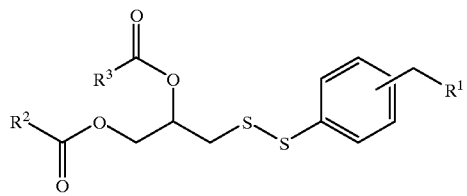

wherein $R^2$ and $R^3$ are hydrocarbons having between about 8 to about 24 carbon atoms.

Figure 7:
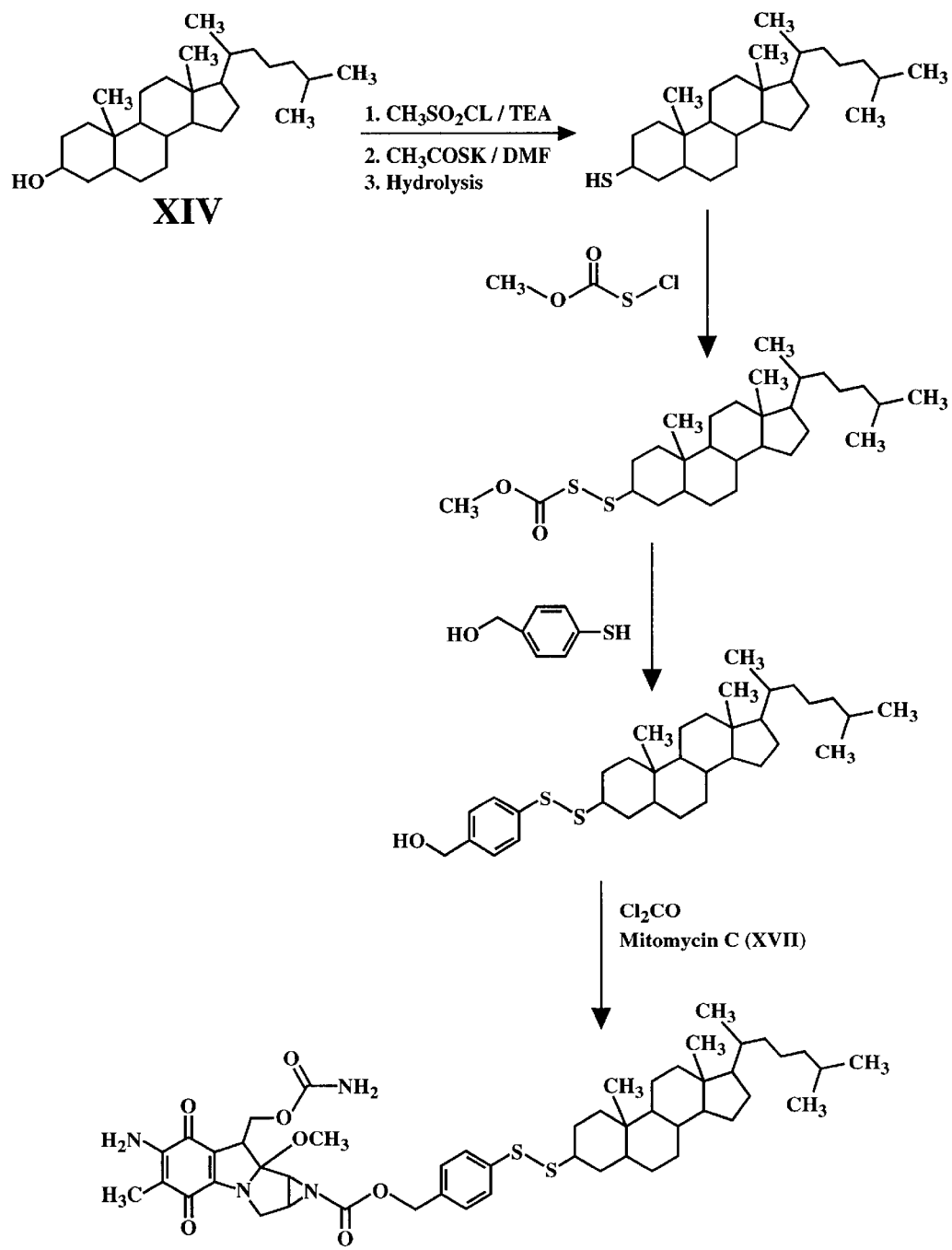
FIG. 7 shows a synthetic reaction scheme for preparation of a cholesterol-dithiobenzyl-mitomycin-C conjugate.

In addition to diacylglycerols as the hydrophobic moiety, other lipids are contemplated. FIG. 7 shows another embodiment where cholesterol is used as the hydrophobic moiety in the conjugate. Cholesterol (Compound XIV) is reacted with methanesulfonyl chloride in dichloromethane in the presence of triethylamine (TEA). The resulting intermediate is then converted into the thiol derivative and ultimately into the principal dithiobenzyl alcohol, which is used to link mitomycin C in a similar fashion as described above for diacylglycerol.

Figure 8:
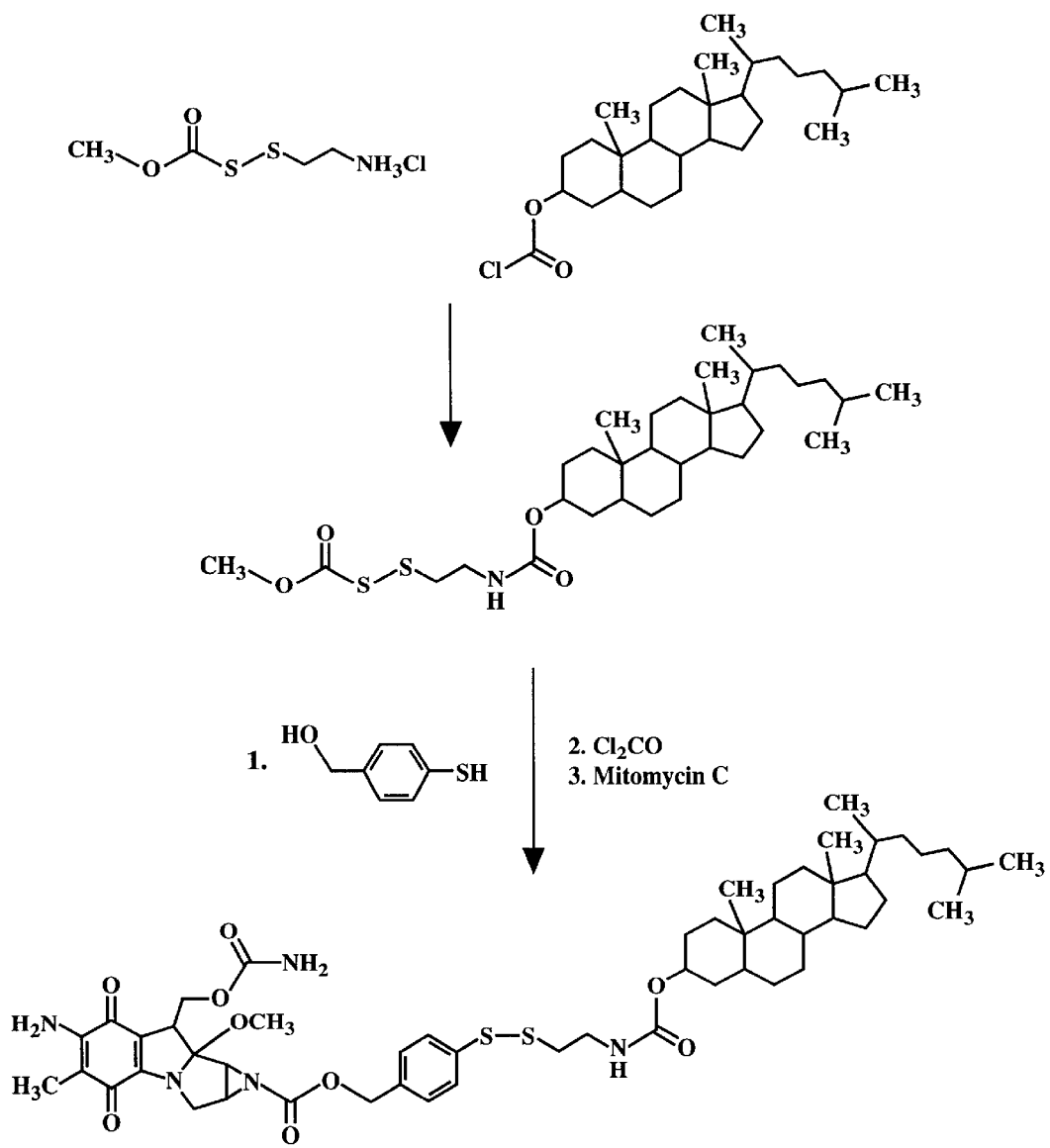
FIG. 8 shows another synthetic reaction scheme for preparation of a cholesterol-dithiobenzyl-mitomycin-C conjugate.

An alternative reaction scheme for preparation of a cholesterol-DTB-mitomycin-C conjugate is shown in FIG. 8. Methoxycarbonyldithioethyl amine is directly reacted with cholesterol chloroformate forming a urethane linkage. Then mercaptobenzylalcohol is used to obtain the DTB-cholesterol compound. Mitomycin C is linked as described above and in Example 2.

Figure 9A:
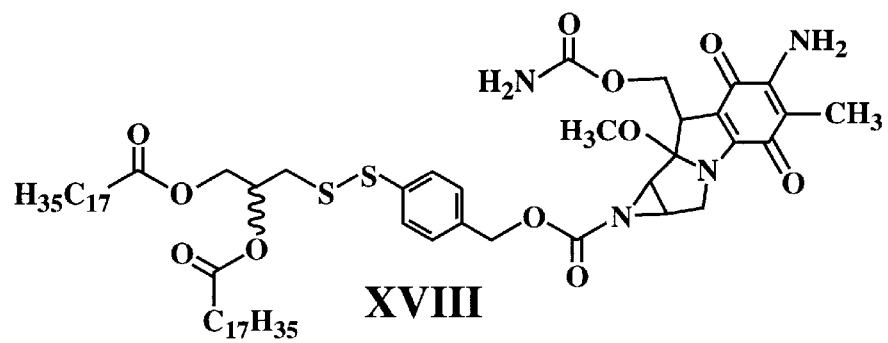
FIGS. 9A–9C show the structures of three lipid-dithiobenzyl-mitomycin-C conjugates, para-distearoyl-DTB-mitomycin-C (FIG. 9A), para-dipalmitoyl-DTB-mitomycin-C (FIG. 9B) and ortho-dipalmitoyl-DTB-mitomycin-C (FIG. 9C)
Figure 9B:
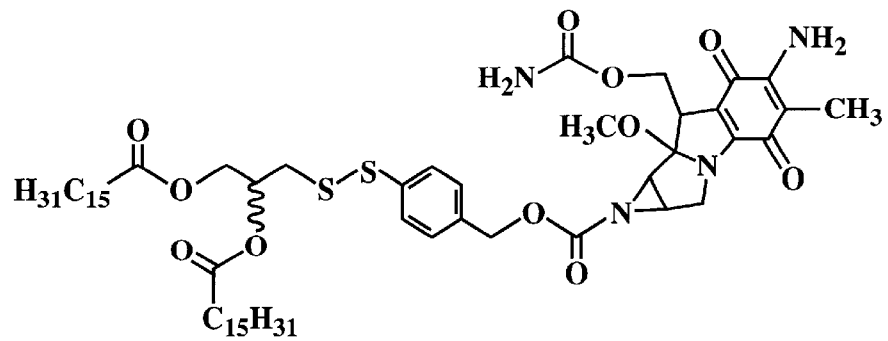
Figure 9C:
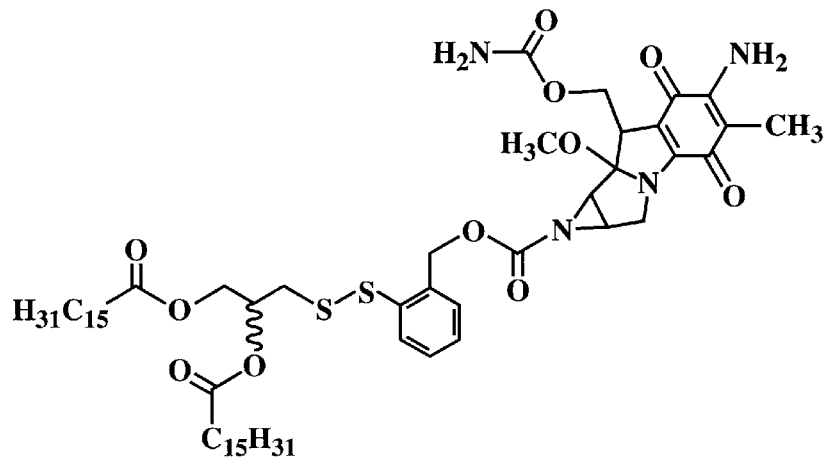

It will be appreciated by one of skill in the art that the various conjugates described above are merely exemplary A wide variety of other hydrophobic moieties and other drugs, such as doxorubicin and daunorubicin, are contemplated and suitable for use in the invention. In additional studies performed in support of the invention, described below, the conjugate prepared as described in FIG. 6A, Compound XVII, para-distearoyl-DTB-mitomycin C, was used. For ease of reference, this conjugate is shown in FIG. 9A. It is to be appreciated that other diacyl lipids, such as a dipalmitoyl lipid, can be used, and FIG. 9B shows a para-dipalmitoyl-DTB-mitomycin C conjugate. It will also be appreciated that the conjugate can also have an isomeric linkage. This is evident by the ortho-dipalmitoyl-DTB-mitomycin C conjugate as shown in FIG. 9C.

III. Preparation of Liposomes Comprising Conjugate

In another aspect, the invention includes a liposome composition comprised of a vesicle-forming lipid and a conjugate as described above. Liposomes are closed lipid vesicles used for a variety of therapeutic purposes, and in particular, for carrying therapeutic agents to a target region or cell by systemic administration of liposomes. In particular, liposomes having a surface coating of hydrophilic polymer chains, such as polyethylene glycol (PEG), are desirable as drug carries as these liposomes offer an extended blood circulation lifetime over liposomes lacking the polymer coating. The polymer acts as a barrier to blood proteins thereby preventing binding of the protein and recognition of the liposomes for uptake and removal by macrophages and other cells of the reticuloendothelial system.

Liposomes, according to the invention, include a conjugate in combination with a lipid, which in one embodiment is a vesicle-forming lipid, and, optionally, other bilayer components. "Vesicle-forming lipids" are lipids that spontaneously form bilayer vesicles in water. The vesicle-forming lipids preferably have two hydrocarbon chains, typically acyl chains, and a polar head group. There are a variety of synthetic vesicle-forming lipids and naturally-occurring vesicle-forming lipids known in the art where the two hydrocarbon chains are typically from about 12 to about 24 carbon atoms in length, and have varying degrees of unsaturation. Examples include the phospholipids, such as phosphatidylcholine (PC), phosphatidylethanolamine (PE), phosphatidic acid (PA), phosphatidylinositol (PI), and sphingomyelin (SM). A preferred lipid for use in the present invention is hydrogenated soy phosphatidylcholine (HSPC). Another preferred family of lipids are diacylglycerols. These lipids can be obtained commercially or prepared according to published methods.

The vesicle-forming lipid may be selected to achieve a degree of fluidity or rigidity, to control the stability of the liposome in serum, and to control the rate of release of an entrapped agent in the liposome. Liposomes having a more rigid lipid bilayer, or a liquid crystalline bilayer, can be prepared by incorporation of a relatively rigid lipid, e.g., a lipid having a relatively high phase transition temperature, e.g., up to about 80° C. Rigid lipids, i.e., saturated, contribute to greater membrane rigidity in the lipid bilayer. Other lipid components, such as cholesterol, are also known to contribute to membrane rigidity in lipid bilayer structures.

Lipid fluidity is achieved by incorporation of a relatively fluid lipid, typically one having a lipid phase with a relatively low liquid to liquid-crystalline phase transition temperature, e.g., at or below room temperature (about 20–25° C.).

The liposome can also include other components that can be incorporated into lipid bilayers, such as sterols. These other components typically have a hydrophobic moiety in contact with the interior, hydrophobic region of the bilayer membrane, and a polar head group moiety oriented toward the exterior, polar surface of the membrane.

Another lipid component in the liposomes of the present invention, is a vesicle-forming lipid derivatized with a hydrophilic polymer. In this lipid component, a derivatized lipid results in formation of a surface coating of hydrophilic polymer chains on both the inner and outer lipid bilayer surfaces. Typically, between about 1–20 mole percent of the derivatized lipid is included in the lipid composition.

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide. The polymers may be employed as homopolymers or as block or random copolymers.

A preferred hydrophilic polymer chain is polyethyleneglycol (PEG), preferably as a PEG chain having a molecular weight between about 500 to about 10,000 Daltons, preferably between about 1,000 to about 5,000 Daltons. Methoxy or ethoxy-capped analogues of PEG are also preferred hydrophilic polymers. These polymers are commercially available in a variety of polymer sizes, e.g., from about 12 to about 220,000 Daltons.

Liposomes of the present invention include typically between about 1 and about 30 mole percent of the lipid-DTB-drug conjugate, preferably between about 5 and about 30 mole percent, more preferably between about 5 and about 20 mole percent. In studies performed in support of the invention, liposomes comprised of the vesicle-forming lipid hydrogenated soy phosphatidylcholine (HSPC), distearoyl phosphatidylethanolamine derivatized with methoxy-polyethylene glycol (mPEG-DSPE) and the conjugate shown in FIG. 9A, para-distearoyl-DTB-mitomycin C (Compound XVIII) were prepared as described in Examples 4A–4B. One of the liposome formulations included cholesterol (Example 4A), with the lipids HSCP/cholesterol/mPEG-DSPE/para-distearoyl-DTB-mitomycin C (Compound XVIII) present at a molar ratio of 60/30/5/5. A second formulation, which contained no cholesterol, was prepared and characterized (Example 4B). In this formulation, the lipids HSCP/mPEG-DSPE/para-distearoyl-DTB-mitomycin C (Compound XVII) were present at a molar ratio of 90/5/5.

IV. In vitro Characterization of Liposomes Containing a Conjugate

A. In vitro Drug Release

Liposomes were prepared as described in Examples 4A–4B and were characterized in vitro to determine the rate of release of mitomycin C following exposure to reducing agent. For the in vitro studies, reducing conditions were induced by addition of cysteine, typically at a concentration of about 150 $\mu$M, to the test medium. It will be appreciated that in vivo, endogenous reducing conditions may be sufficient to effect thiolytic decomposition of the lipid-DTB-drug conjugate for release of the drug. It is further contemplated that reducing conditions in vivo can be artificially induced by administration of a suitable reducing agent, such as cysteine or glutathione.

The liposome formulations, e.g., HSPC/cholesterol/mPEG-DSPE/conjugate Compound XVIII (hereinafter the "cholesterol-containing formulation") and HSPC/mPEG-DSPE/conjugate Compound XVIII (hereinafter the "cholesterol-free liposome formulation") were incubated at 37° C. in the presence of 150 $\mu$M cysteine for 24 hours. Samples were withdrawn at selected time points and analyzed by high performance liquid chromatography (HPLC) to quantify the amount of conjugate and of free mitomycin C. The HPLC conditions are described in Example 5.

Figure 10A:
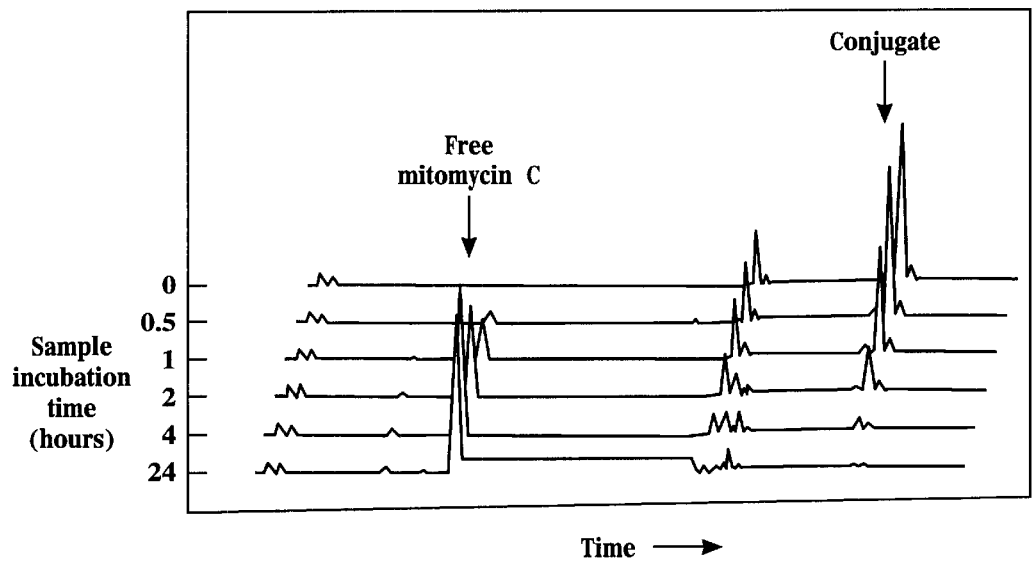
FIGS. 10A–10B are HPLC chromatograms for liposomes comprised of HSPC/mPEG-DSPE/lipid-DTB-mitomycin C (FIG. 10A) and HSPC/cholesterol/mPEG-DSPE/lipid-DTB-mitomycin C (FIG. 10B), where each figure shows a series of chromatograms as a function of time of incubation of the liposomes in the presence of cysteine.
Figure 10B:
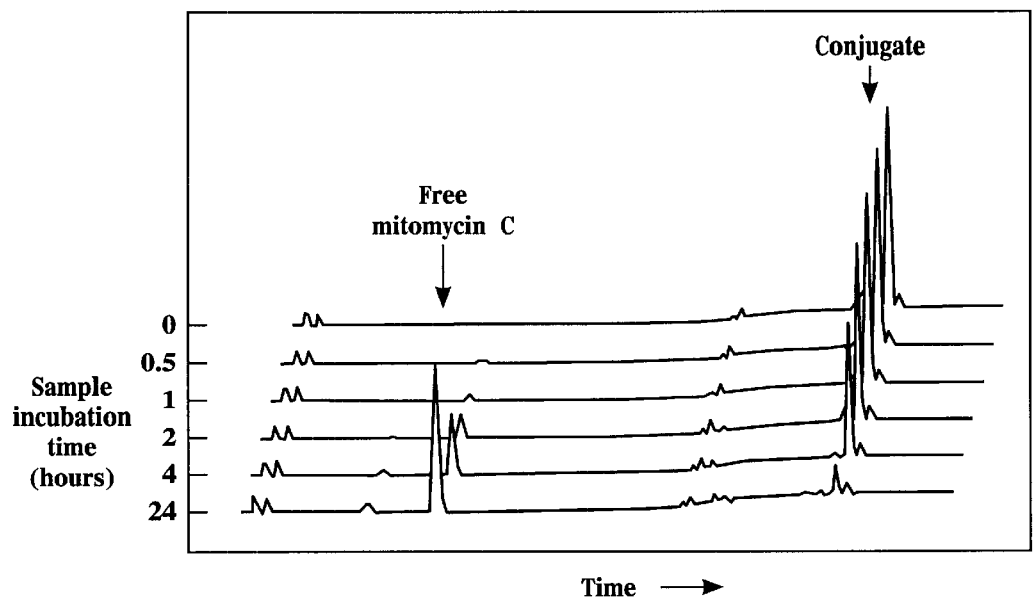

FIGS. 10A–10B show HPLC chromatograms for two liposome formulations. In FIG. 10A, the results for the cholesterol-free liposome formulation are shown. At time zero, there is no detectable free mitomycin C and all measurable drug is in the form of a lipid-DTB-drug conjugate that is liposome bound. As the incubation time increases, the amount of mitomycin C released from the liposomes and detectable in free form increases, with a corresponding decrease in the presence of conjugate-bound mitomycin C.

FIG. 10B shows the result, for the liposome formulation containing cholesterol. In the first sample taken at time zero, there was no detectable free mitomycin C. After 1 hour of incubation in 150 $\mu$M cysteine, a small amount of free drug was detected, indicating decomposition of the liposome-bound lipid-DTB-mitomycin conjugate. In comparison with FIG. 10A, liposomes containing cholesterol yield a slower conjugate decomposition rate and accordingly slower release of the drug.

Figure 11:
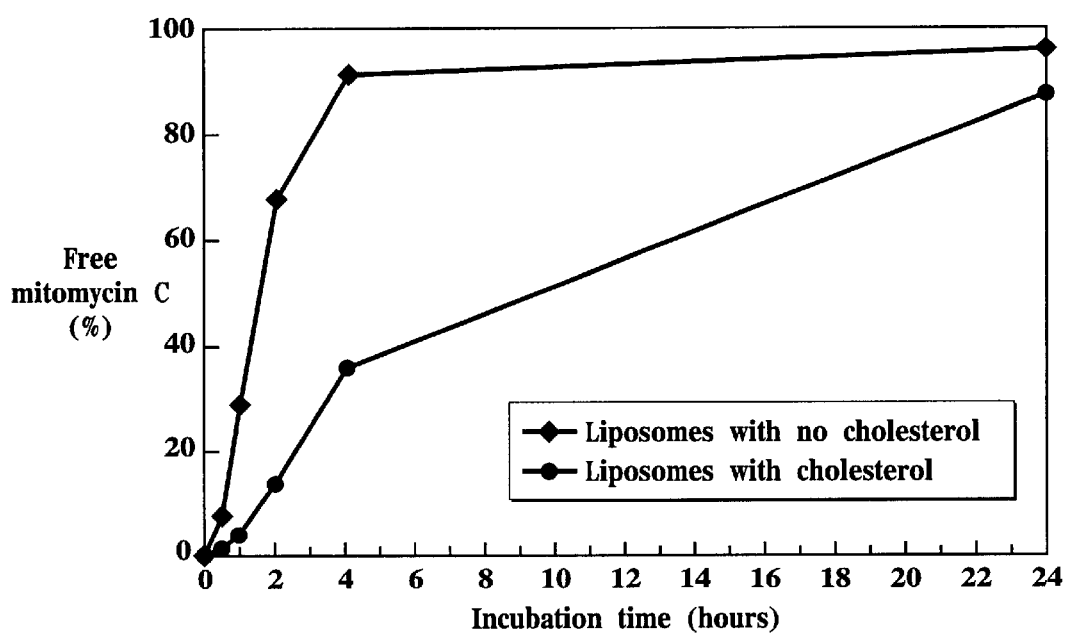
FIG. 11 is a plot showing the percent of mitomycin C released from liposomes comprised of HSPC/mPEG-DSPE/lipid-DTB-mitomycin C (closed diamonds) and HSPC/cholesterol/mPEG-DSPE/lipid-DTB-mitomycin C (closed circles) as a function of time of incubation in the presence of cysteine.

FIG. 11 is a plot showing the percent of mitomycin C released from the two liposome formulations, as determined from the chromatograms in FIGS. 10A–10B. The cholesterol-free liposomes (closed diamonds) had a higher rate of release than the liposomes containing cholesterol (closed circles). More than 50% of the mitomycin C was released from the liposome-bound conjugate after 2 hours for the cholesterol-free formulation. For both formulations, greater than 80% of the drug was released at the end of the 24 hour incubation period.

Figure 12A:
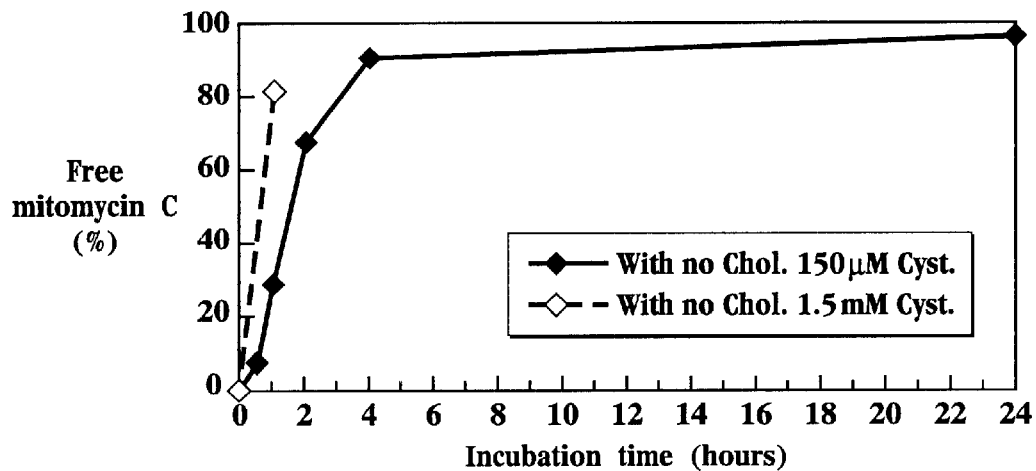
FIGS. 12A–12B are plots showing the percent of mitomycin C released from liposomes comprised of HSPC/mPEG-DSPE/lipid-DTB-mitomycin C (FIG. 12A) and HSPC/cholesterol/mPEG-DSPE/lipid-DTB-mitomycin C (FIG. 12B) as a function of time of incubation in the presence of cysteine at concentrations of 150 μM (closed symbols) and at 1.5 mM (open symbols)
Figure 12B:
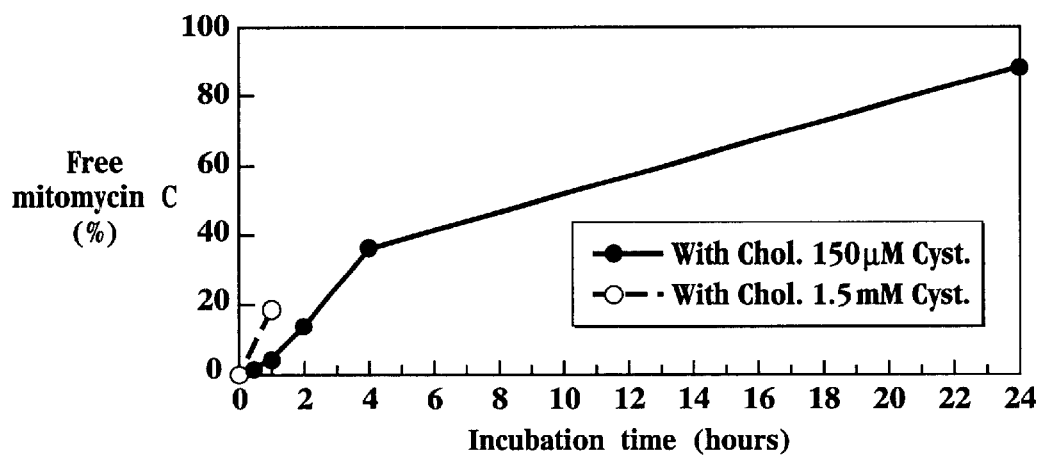

In another study, the two liposome formulations were incubated in 1.5 mM cysteine. Analysis was done as described in Example 5 and the results are shown in FIGS. 12A–12B. FIG. 12A shows the percent of mitomycin C released from the lipid-DTB-drug conjugate incorporated into the cholesterol-free liposomes (HSPC/PEG-DSPE/lipid-DTB-mitomycin C). The percent release during incubation with 150 $\mu$M are also shown (closed diamonds) for comparison. As seen, incubation at a higher concentration of reducing agent (1.5 mM, open diamonds) causes an increase in the rate of conjugate decomposition and rate of drug release.

FIG. 12B shows the results for the liposome formulation containing cholesterol. Liposomes incubated in 1.5 mM (open circles) have a significantly higher decomposition rate than the same liposomes incubated in 150 $\mu$M cysteine (closed circles).

B. In vitro Cytotoxicity

The in vitro cytotoxicity of liposomes containing the lipid-DTB-mitomycin C conjugate (Compound XVIII) was evaluated using M-109 cells, a mouse lung carcinoma line. As described in Example 6, M109 cells were incubated in the presence of free mitomycin C or liposomes containing the distearoyl-DTB-mitomycin C conjugate. Liposomes prepared as described in Examples 4A–4B with the molar ratios specified in Example 6A were tested. Cysteine at concentrations of 150 μM, 500 μM and 1000 μm was added to some of the test cells to effect thioytic decomposition of the conjugate and release of mitomycin C.

IC50 values were taken as the drug concentration which caused a 50% inhibition of the control growth rate ($IC_{50}$), as described in Example 6. The results are shown in Table 1.

TABLE 1

$IC_{50}$ Values for M109 tumor cells after 72 hour culture with continuous exposure to formulation

| Formulation | Cysteine Concentration | | | |
| --- | --- | --- | --- | --- |
|  | 0 | 150 μM | 500 μM | 1000 μM |
| free MMC[1] | 285 ± 92 | n.d.[4] | n.d. | 300 ± 71 |
| liposomes with cholesterol[2] | 1750 ± 356 | 1140 ± 368 | 650 ± 42 | 510 ± 113 |
| cholesterol-free liposomes[3] | 5400 ± 1414 | 4550 ± 1484 | 3600 ± 1272 | 2550 ± 778 |

Figure 13:
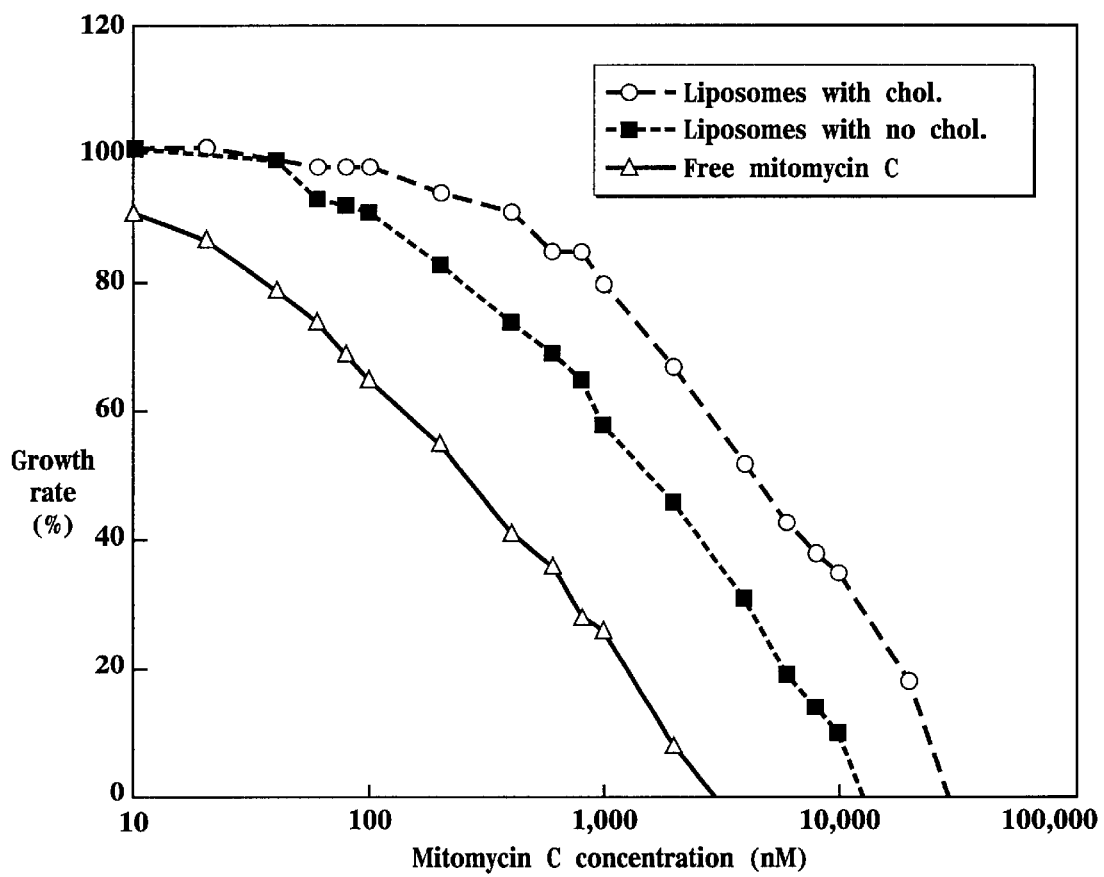
FIG. 13 is a plot of growth rate of M109 cells, expressed as a percentage based on growth of M109 cells in the absence of drug and cysteine, as a function of mitomycin C amount, in nM, for free mitomycin c (open triangles), liposomes comprised of HSPC/mPEG-DSPE/lipid-DTB-mitomycin C (closed squares), and liposomes comprised of HSPC/cholesterol/mPEG-DSPE/lipid-DTB-mitomycin C (open circles)

[1]MMC = mitomycin C
[2]HSPC/cholesterol/mPEG-DSPE/distearoyl-DTB-MMC (90/45/5/5)
[3]HSPC/mPEG-DSPE/distearoyl-DTB-MMC (90/5/5)
[4]n.d. = not done The percent growth rate of M109 mouse carcinoma cells determined from the cytotoxicity studies is shown in FIG. 13. The percent growth rate is expressed as a percentage based on growth rate of M109 cells in the absence of mitomycin C and of cysteine and is shown as a function of mitomycin C concentration, in nM. The growth rate of cells was determined as described in Example 6. As seen, the percent of cell growth rate decreases as the cysteine concentration is increased for both the liposomes containing cholesterol (open circles) and the cholesterol-free liposome formulation (closed squares). It can also be seen that cysteine e has n o effect on the activity of free mitomycin c and that mitomycin C is released from the conjugate to effectively inhibit cell growth.

Figure 14A:
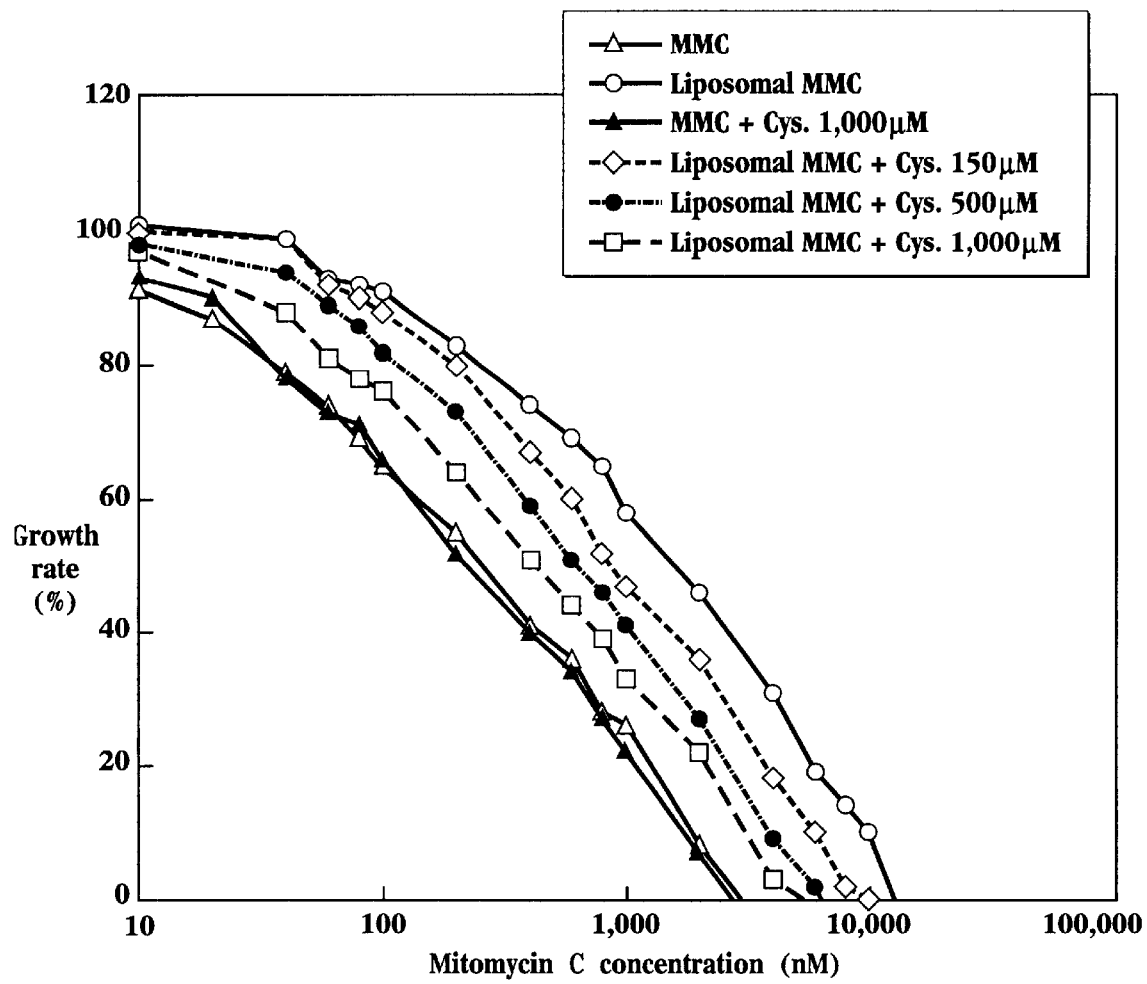
FIG. 14A is a plot of growth rate of M109 cells, expressed as a percentage based on growth of M109 cells in the absence of drug or cysteine, as a function of mitomycin C concentration in nM. Shown are cells treated mitomycin C in free form (open triangles) and with mitomycin C in free form plus 1000 μM cystein (closed triangles). Also shown are cells treated with the liposome formulation comprised of HSPC/PEG-DSPE/lipid-DTB-mitomycin C (open circles) and with the liposome formulation with additional cysteine added at concentrations of 150 μM (open diamonds), 500 μM (closed circles) and 1000 μM (open squares)
Figure 14B:
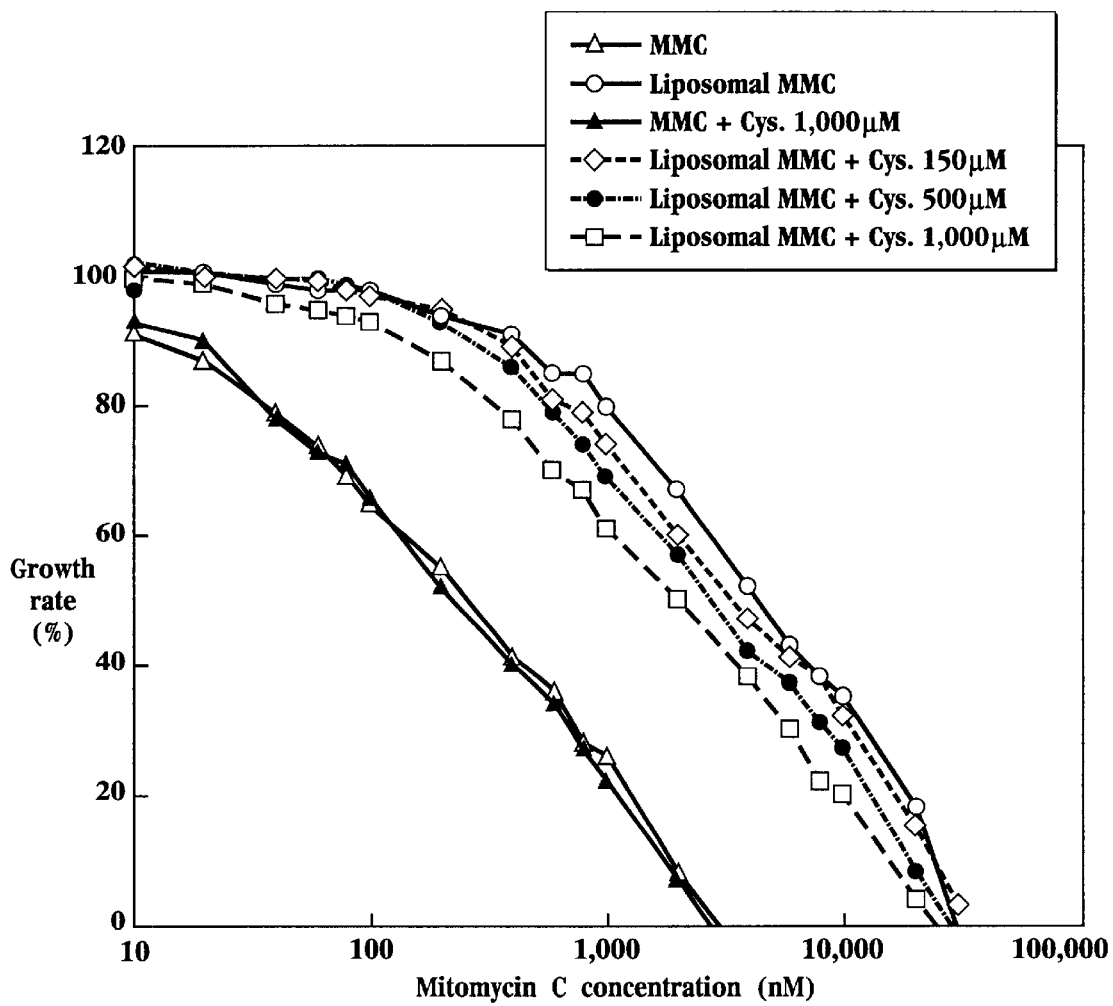
FIG. 14B is a plot of growth rate of M109 cells, expressed as a percentage based on growth of M109 cells in the absence of drug or cysteine, as a function of mitomycin C concentration in nM. Shown are cells treated mitomycin C in free form (open triangles) and with mitomycin C in free form plus 1000 μM cystein (closed triangles). Also shown are cells treated with the liposome formulation comprised of HSPC/cholesterol/mPEG-DSPE/lipid-DTB-mitomycin C (open circles) and with the liposome formulation with additional cysteine added at concentrations of 150 μM (open diamonds), 500 μM (closed circles) and 1000 μM (open squares)

The in vitro growth rate of M109 mouse carcinoma cells treated with mitomycin C in free form or with mitomycin C in the form a liposome-bound lipid-DTB-drug conjugate is shown in FIGS. 14A–14B. In FIG. 14A the results for the liposome formulation containing no cholesterol are shown. In the plot, the growth rate of M109 cells is expressed as a percentage based on growth of M109 cells in the absence of drug and cysteine and is shown as a function of mitomycin C concentration in nM. The cells treated with mitomycin C in free form (open triangles) and with mitomycin C in free form plus 1000 μM cysteine (closed triangles) exhibit a decrease in growth rate due the toxicity of the drug in free form. Cells treated with the liposome formulation comprised of HSPC/PEG-DSPE/DSPE-DTB-mitomycin C (open circles) and with the liposome formulation with additional cysteine added at concentrations of 150 μM (open diamonds), 500 μM (closed circles) and 1000 μM (open squares) exhibited cell cytotoxicity in a cysteine-dose dependent fashion.

FIG. 14B is a similar plot for the liposome formulation containing cholesterol. The same pattern was observed for cells treated with the liposome composition containing cholesterol plus additional cysteine at concentrations of 150 μM (open diamonds), 500 μM (closed circles) and 1000 μm (open squares). That is, as the concentration of cysteine increased, the cell growth rate decreased. This indicates a cysteine-induced release of mitomycin C in direct correlation with cysteine concentration. In contrast to the liposome formulations, the in vitro growth rate of cells treated with mitomycin C in free form (open triangles) was the same as the growth rate of cells treated with mitomycin C in free form plus 1000 μM cysteine (closed triangles).

Figure 15:
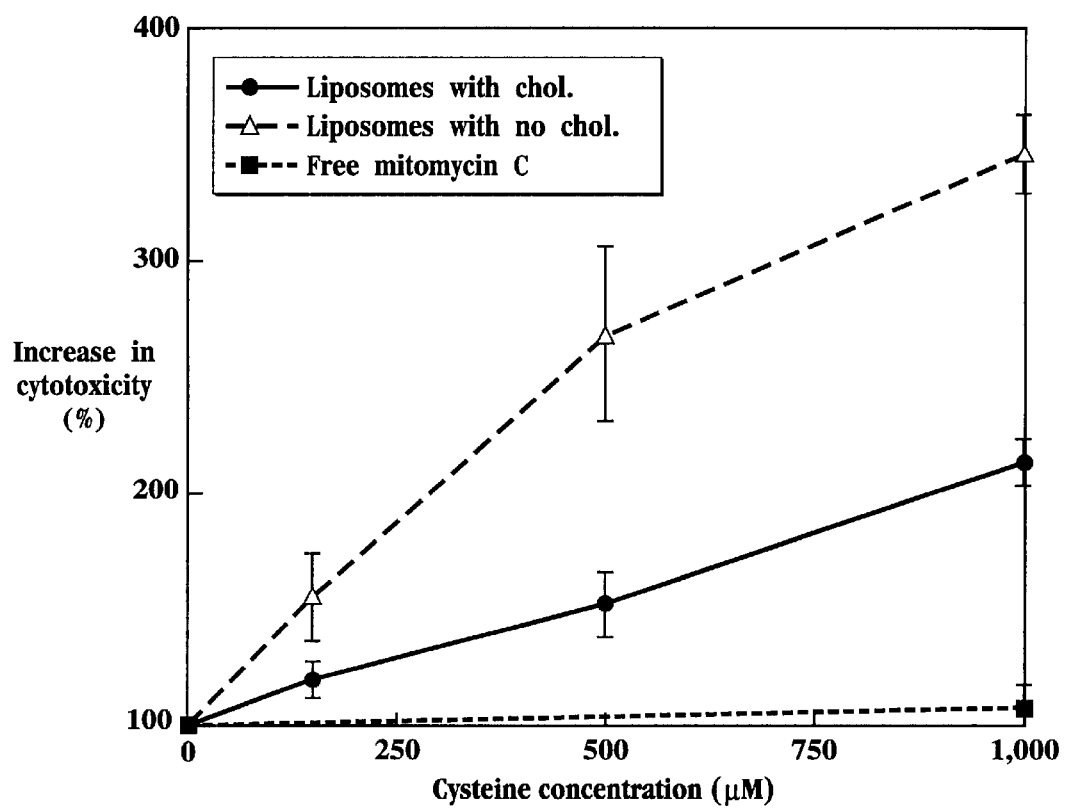
FIG. 15 is a plot showing the percent increase in cytotoxicity (as determined by ($IC50_{no\ cysteine}/IC50_{cysteine}$)×100) of free mitomycin C (closed squares), mitomycin C associated with liposomes comprised of HSPC/cholesterol/mPEG-DSPE/lipid-DTB-mitomycin C (closed circles), and liposomes comprised of HSPC/mPEG-DSPE/lipid-DTB-mitomycin C (open triangles) to M109 cells in vitro at various concentrations of cysteine.

FIG. 15 shows the percent increase in cytotoxicity as a function of cysteine concentration, in μM, of free mitomycin C and of the liposome formulations. Increase in cytotoxicity was determined by the percent drop in IC50, e.g., IC50 in the presence of cysteine relative to IC50 in the absence of cysteine time 100 (($IC50_{no\ cysteine}/IC50_{cysteine}$)×100)). As seen, the percent of cytotoxicity increases significantly as the cysteine concentration is increased for both the liposomes containing cholesterol (open triangles) and the cholesterol-free liposome formulation (closed circles). Cytotoxicity of free mitomycin C (closed squares) is not effected by the presence of cysteine.

The cytotoxicity data shows that the cholesterol-free liposome formulation is more affected by cysteine. The IC50 of the cholesterol-free liposome formulation at certain cysteine concentrations is only 2-fold lower than that of the free drug alone. The liposome formulation containing cholesterol is less cytotoxic than the cholesterol-free liposome formulation. The data also shows that cysteine has no cytotoxic effect of the tumor cells and no effect on the cytotoxicity of free mitomycin C. It is also apparent from the data that cysteine increases in a dose-dependent fashion the cytotoxicity of liposome-bound mitomycin C. Thus, the cytotoxic effects observed for the liposomal formulations are mostly accounted for by cysteine-mediated release of mitomycin C from the lipid-DTB-drug conjugate.

C. In vivo Pharmacokinetics

The in vivo pharmacokinetics of the liposomes containing cholesterol and the cholesterol-free liposome formulation was determined in rats. As described in Example 7, the animals were treated with a single bolus intravenous injection of approximately 0.1 mg/mL mitomycin C in free form or incorporated into liposomes in the form of the lipid-DTB-mitomycin C conjugate in accord with the invention. After injection, blood samples were taken and analyzed for amount of mitomycin C. The results are shown in FIGS. 16A–16B.

Figure 16A:
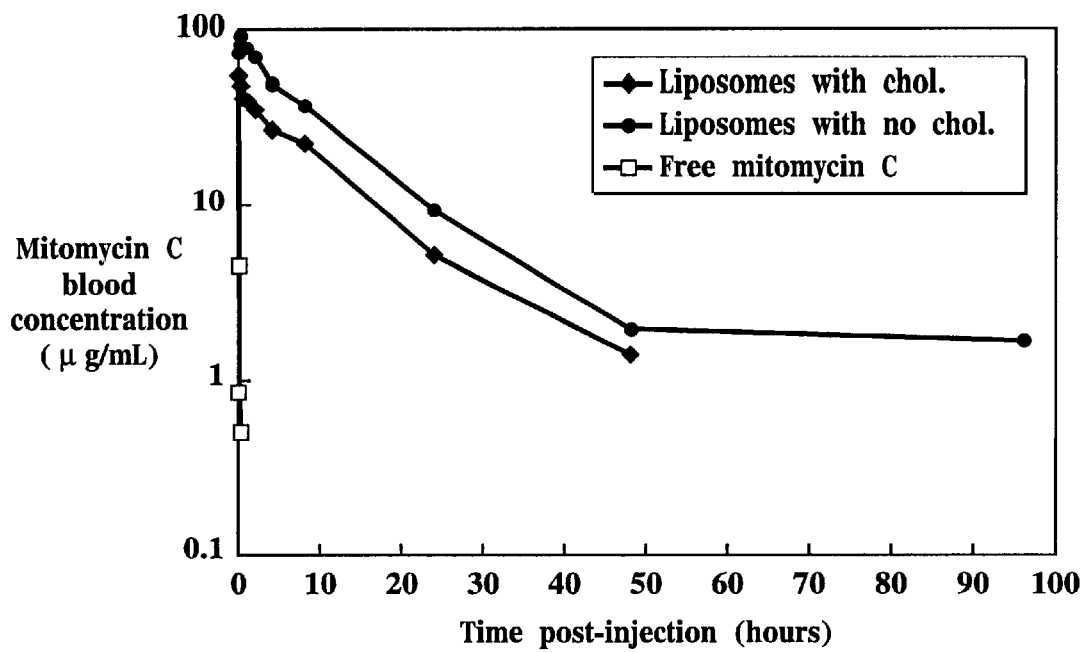
FIG. 16A is a plot showing the concentration of mitomycin C in the blood of rats as a function of time in hours following intravenous injection of free mitomycin C (open squares), liposomes comprised of HSPC/cholesterol/mPEG-DSPE/lipid-DTB-mitomycin C (closed diamonds), and liposomes comprised of HSPC/mPEG-DSPE/lipid-DTB-mitomycin C (closed circles)

FIG. 16A shows the concentration (μg/mL) of mitomycin C in the blood of rats as a function of time in hours following intravenous injection. As seen, free mitomycin C (open squares) administered intravenously in free form is rapidly cleared from the blood. Mitomycin C in the form of a liposome-bound lipid-DTB-drug conjugate remains in circulation for a substantially longer period of time. Mitomycin C associated with liposomes containing cholesterol (closed diamonds) and with cholesterol-free liposomes (closed circles) was detected in the blood at greater than 10 μg/mL for 20–25 hours.

Figure 16B:
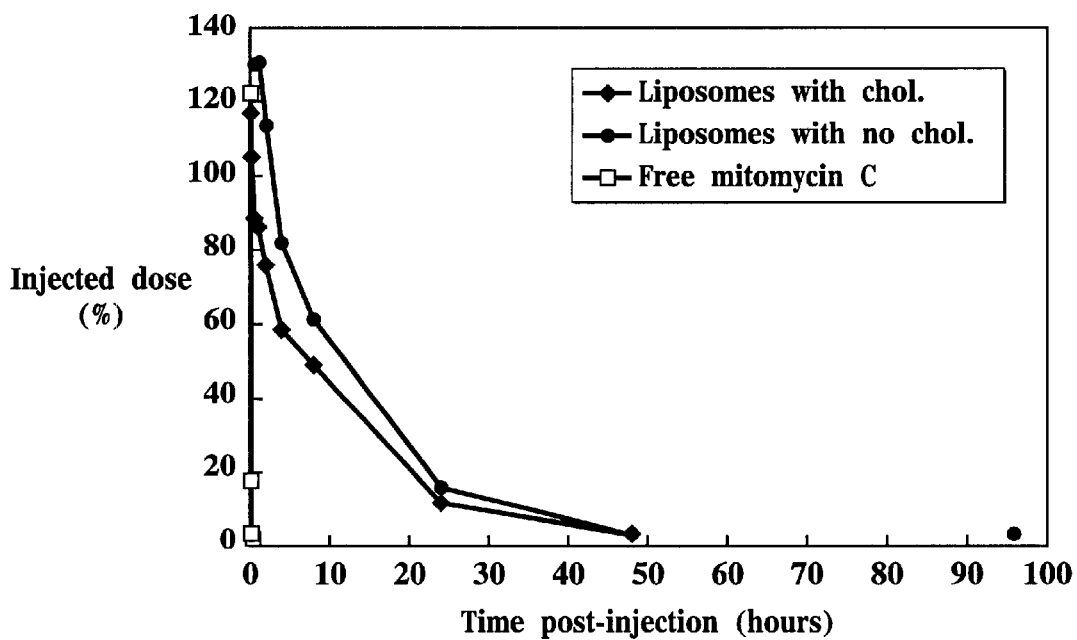
FIG. 16B is a plot showing the percent of injected dose remaining in the blood of rats as a function of time in hours following intravenous injection of free mitomycin C (open squares), liposomes comprised of HSPC/cholesterol/mPEG-DSPE/lipid-DTB-mitomycin C (closed diamonds), and liposomes comprised of HSPC/mPEG-DSPE/lipid-DTB-mitomycin C (closed circles).

FIG. 16B shows the percent of injected dose remaining in the blood as a function of time in hours following intravenous injection of the test formulations. Virtually none of the dose of free mitomycin C (open squares) remains in the blood at time points greater than about 5 minutes. However, at 20 hours after injection of the liposome formulations, about 15–18 percent of the dose of mitomycin C remains in circulation. This indicates the mitomycin C-DTB-lipid conjugate remains stable in the liposome while in circulation and that minimal thiolytic cleavage occurs in plasma. Therefore, this system appear to be compatible with long-circulating liposomes (Stealth® liposomes) which have an extended blood circulation lifetime and enhanced accumulation in tumors.

V. EXAMPLES

The following examples further illustrate the invention described herein and are in no way intended to limit the scope of the invention.

Materials

All materials were obtained from commercially suitable vendors, such as Aldrich Corporation.

Example 1

Synthesis of para-diacyldiglyceroldithiobenzalcohol (Compound IV) and ortho-diacyldiglyceroldithiobenzalcohol A. para-diacyldiglyceroldithiobenzalcohol This reaction is illustrated in FIG. 1. The procedure of Snyder, W. R. (*Journal of Lipid Research*, 28:949 (1987) was followed to prepare Compounds II and III.

A 100 ml round bottom flask containing 3-mercapto-1,2-propanediol (Compound I, 1 g, 9.26 mmol) in 5 ml of water was placed in an ice-bath. To this rapidly stirring flask, hydrogenperoxide (exactly 0.5 mole equivalent, 525 $\mu$l, 4.63 mmol) was dropwise added while maintaining the temperature between 30–40° C. At the end of the exothermic process, the reaction was allowed to stir overnight at room temperature. Water was azeotroped with rotary evaporation by successive addition of acetonitrile in 20 ml aliquots. The process of acetonitrile addition was repeated 3–4 times or until all water was removed, yielding a clear oil. After scratching the flask with a metal spatula and cooling overnight at −20° C., the oily product solidified (Compound II, rac-3,3'-dithiobis(1,2-propanediol)). The chalky solid was dried in vacuo over $P_2O_5$. Yield: 630 mg, 63%. $^1$HNMR ($CD_3OD$, 360 MHz) $\delta$ 2.77, 2.95 (2×d, $CH_2OH$, 2H), 3.59 (M, $SCH_2$, 2H), 3.87 (m, CH, 1H) ppm.

The rac-3,3'-dithiobis(1,2-propanediol) product (Compound II) was acylated by adding the compound (980 mg, 4.6 mmol) to an oven-dried 100 mL round bottom flask and dissolving in dry methylene chloride (40 mL). To this, stearic acid (4.92 g, 17.1 mmol) and 4-dimethylamino) pyridinium 4-toluenesulfonate (1.38 g, 4.6 mmol) as the catalyst was and stirred at room temperature (25° C.) for 20 minutes. Then diisopropylcarbodiimide (3.1 mL, 20 mmmol) was pipetted and reacted overnight at room temperature. TLC silic on GF (10% ethylacetate in hexane) showed the complete reaction of the diol group. (rac-3,3'-dithiobis(1,2-propanediol) $R_f$=0.60; rac-3,3'-dithiobis(1,2-propanedistearoyl) $R_f$=0.35). Amberlyst® A-21 slightly basic ion-exchange resin (~3 g) and Amberlyst® 15 strongly acidic ion-exchange resin (~3 g) were added to the reaction mixture. After 30 minutes of shaking, the resins were filtered and the filtrate was taken to dryness. The residue was recrystallized from isopropanol three time (100 mL each). The solid product, rac-3,3'-dithiobis(1,2-propanedistearoyl) (Compound III), was collected and dried over $P_2O_5$. Yield: 70%, 4.1 g. Melting Point 54–55° C. $^1$HNMR ($CDCl_3$, 360 MHz) $\delta$ 0.86, (t, $CH_3$, 6H), 1.22 (s, lipid, 56H), 1.48 (m, $CH_2CH_2(CO)O$, 4H), 2.26 (2×t, $CH_2(CO)O$, 4H), 2.87 (d, $CH_2S$, 2H), 4.03 & 4.22 (2×d, $CH_2CH$ of lipid, 2H), 4.97 (m, $CHCH_2$ of lipid)ppm.

In the next step, a solution of rac-3,3'-dithiobis(1,2-propanedistearoyl) (Compound III) (2.97 g, 2.33 mmol) was dissolved in toluene (30 mL) and placed in an ice bath. Sulfuryl chloride (1.9 mL, 23.2 mmol) was pipetted into the flask and the mixture was stirred at the cold ice bath temperature for 30 minutes. The flask was then placed at room temperature and stirred for another 30 minutes. Excess of sulfuryl chloride was removed with a rotary evaporator. A fresh (20 mL) aliquot of toluene was added to the reaction flask and placed on an ice bath. To this, a solution of 4-mercaptobenzalcohol (780 mg, 5.6 mmol) in toluene was added with a slow rate. After 5 hours of reaction time, all solvents were evaporated with rotary evaporation to dryness. Warm ethyl acetate (10 mL) was added to the reaction flask to dissolve the solid and insoluble matter was filtered. To the ethyl acetate solution, 50 mL of ether was added to precipitate, and the solid product (para-diacyl-diglycerol-dithiobenzalalcohol, Compound IV) was collected by filtration. This process was repeated twice. Yield: 75%.

To purify the product (para-diacyl-diglycerol-dithiobenzal-alcohol, Compound IV), a silica gel column (20×2.5 cm) in chloroform was prepared. The sample was dissolved in minimum amount of chloroform and was chromatographed with addition of two different mobile phases. First, 100% $CHCl_3$ (100 ml) was eluted. This fraction contained the impurity dithiobenzyl alcohol. The confirmation was made by $^1$HNMR. Then, Changing the mobile phase to 15% methanol in chloroform, the pure product was collected by flash chromatography. By eluting 500 ml of $CH_3OH$:$CHCl_3$ (15:85) pure DGTBA (one spot by TLC) was collected. After evaporation of the solvents, the solid was lyophilized from t-BuOH and dried in vacuo over $P_2O_5$. The final purification dropped the yield to 40%, 1.4 g. $^1$HNMR: ($CDCl_3$, 360 MHz) $\delta$ 0.86 (t, $CH_3$, 6H), 1.22 (s, lipid, 56H), 1.48 (m, $CH_2CH_2(CC)O$, 4H), 2.26 (2×t, $CH_2(CO)O$, 4H), 2.87 (d, $CH_2S$, 2H), 4.03 & 4.22 (2×d, $CH_2CH$ of lipid, 2H), 4.69 (s, $CH_2$, bz, 2H), 4.97 (m, $CHCH_2$ of lipid), 7.36 & 7.56 (d, $CH_2$, aromatic, 4H) ppm.

5 mg of sample was submitted to a laboratory for elemental analysis (Midwest Micro Lab).

| Analysis | Theoretical | Measured |
|---|---|---|
| Carbon | 70.93% | 70.67% |
| Hydrogen | 10.50% | 10.41% |
| Sulfur | 8.25% | 8.31% |

B. ortho-diglyceroldithiobenzalcohol

A solution of rac-3,3'-dithiobis(1,2-propanedistearoyl) (Compound III) (200 mg, 0.156 mmol) was dissolved in toluene (30 mL) and placed in an ice bath. Sulfuryl chloride (39 $\mu$l, 0.47 mmol) was pipetted into the flask and the mixture was stirred at the cold ice bath temperature for 30 minutes. The flask was then placed at room temperature and stirred for another 30 minutes. Excess of sulfuryl chloride was removed with a rotary evaporator. A fresh (20 mL) aliquot of toluene was added to the reaction flask and placed on an ice bath. To this, a solution of 2-mercaptobenzalcohol (48 mg, 35 mmol) in toluene was added with a slow rate. After 5 hours of reaction time, all solvents were evaporated with rotary evaporation to dryness. Warm ethyl acetate (10 mL) was added to the reaction flask to dissolve the solid and insoluble matter was filtered. To the ethyl acetate solution, 50 mL of ether was added to precipitate, and the solid product (ortho-diacyl-diglycerol-dithiobenzalalcohol) was collected by filtration. This process was repeated twice. The solid was dried in vacuo over $P_2O_5$. Yield: 75%, 190 mg. $^1$HNMR: ($CDCl_3$, 360 MHz) $\delta$ 0.86 (t, $CH_3$, 6H), 1.25 (s, lipid, 56H), 1.58 (m, $CH_2CH_2(CO)O$, 4H), 2.28 (2×t, $CH_2(CO)O$, 4H), 2.91 (d, CH2S, 2H), 4.14 & 4.35 (2×d, $CH_2CH$ of lipid, 2H), 4.86 (s, CH2, bz, 2H), 5.26 (m, $CHCH_2$ of lipid), 7.31 (m, aromatic, 2H), 7.48 & 7.75 (d, aromatic, 2H) ppm.

Example 2

Synthesis of para-diacyldiglyceroldithiobenzal-mitomycin C (Compound XVIII)

This reaction is illustrated in FIG. 6A.

A 50 mL round bottom flask was charged with phosgene (3.1 mmol) and toluene (5 mL) and the solution was cooled to 0° C. A solution of para-diacyl-diglycerol-dithiobenzal-alcohol, (Compound IV, prepared as described in Example 1, 0.31 mmol) in toluene (2.5 mL) was prepared. The alcohol solution was then added dropwise to the phosgene solution. The mixture was allowed to warm to room temperature overnight. After 18 hours, the solution was concentrated in vacuo to remove excess phosgene. The crude acyl chloride was redissolved in toluene (5 mL).

A solution of mitomycin C (0.31 mmol), dimethylaminopyridine (0.031 mmol) and DMF (1 mL) was prepared. The mitomycin C solution was added drop-wise the acyl chloride solution. After 1 hour, the toluene was evaporated off and the crude product was chromatographed (1:1 hexane:ethyl acetate) on silica. The purified product was then taken up in t-BuOH (50 mL) and lyophilized. The product was a purple solid (183 mg, 53%). $R_f$=0.38 (50% hexane: ethyl acetate); $^1$H NMR (360 MHz, CDCl$_3$) δ 0.88 (t, J=6.8 Hz, 6H), 1.26 (s, 58 H), 1.58–1.63 (m, 4H), 1.76 (s, 3H), 2.29 (t, J=7.6 Hz, 4H), 2.93–2.96(m, 2H), 3.19 (s, 3H), 3.29 (dd, ,J=4.7 and 2.9 Hz, 1H), 3.41 (dd, J=5.0 and 2.2 Hz, 1H), 3.48 (dd, J=13.7 and 2.5 Hz, 1H), 3.67 (dd, J=11.5 and 4.7 Hz, 1H), (ddd, J=12.2 and 5.8 and 2.5 Hz, 1H), 4.27–4.36 (m, 2H), 4.43 (d, J=13.3Hz, 1H), 4.61 (s, 2H), 4.90 (ddd, J=10.4 and 5.0 and 2.2 Hz, 1H), 5.00–5.12 (m, 3H), 5.26–5.30 (m, 1H), 7.32 (d, J=8.6 Hz, 2H), 7.50 (d, J=7.9 Hz, 2H); MALDI MS calcd for $C_{62}H_{99}N_4O_{11}S_2Na$: 1164, found m/z 1164 (M+Na).

Example 4

Liposome Preparation

A. Liposomes Containing Cholesterol

1. Liposome Preparation 59 mg HSPC, 14.4 mg cholesterol, 17.4 mg mPEG-DSPE, and 7.4 mg para-distearoyl-DTB-mitomycin C (molar ratio of 60/30/5/5) were added to 1 mL dehydrated ethanol at 60–65° C. and mixed until dissolved, approximately 10 minutes.

A hydration medium composed of 10 mM histidine and 150 mM NaCl in distilled water was warmed to 70° C.

The warm lipid solution was rapidly added to the warm (63–67° C.) hydration medium, with mixing, to form a suspension of liposomes having heterogeneous sizes. The suspension was mixed for one hour at 63–67° C.

2. Extrusion

The liposomes were sized to the desired mean particle diameter by controlled extrusion through polycarbonate filter cartridges housed in Teflon-lined stainless steel vessels. The liposome suspension was maintained at 63–65° C. throughout the extrusion process, a period of 6–8 hours.

3. Diafiltration

Ethanol was removed from the liposome suspension by diafiltration. A histidine/sodium chloride solution was prepared by dissolving histidine (10 mM) and sodium chloride (150 mM) in sterile water. The pH of the solution was adjusted to approximately 7. The solution was filtered through a 0.22 μm Durapore filter. The liposome suspension was diluted in approximately a 1:1 (v/v) ratio with the histidine/sodium chloride solution and diafiltered through a polysulfone hollow-fiber ultrafilter. Eight volume exchanges were performed against the histidine/sodium chloride solution to remove the ethanol. The process fluid temperature was maintained at about 20–30° C. Total diafiltration time was approximately 4.5 hours.

4. Sterile Filtration

The liposome suspension was heated to 33–38° C. and filtered through a 0.2 μm Gelman Supor polyethersulfone filter. Total filtration time was approximately 10 minutes.

After each processing step (hydration, extrusion, dialysis and filtration) the lipid concentration and conjugate/drug concentration were determined by HPLC. Liposome particle size was measured by dynamic light scattering and the amount of "free", unbound mitomycin C in the external suspension medium was measured by HPLC.

| | lipid-DTB-MMC[1,2] Conjugate | lipid | conjugate/ lipid ratio | Liposome Size (nm) | | free MMC[2] |
|---|---|---|---|---|---|---|
| | (μg/mL) | (mg/mL) | | 90° | 30° | (%) |
| post-hydration | 699 | 12.50 | 56 | — | — | 2 |
| post-extrusion | 369 | 8.49 | 43 | 105 | 186 | 4 |
| post-dialysis | 311 | 7.78 | 40 | — | — | 0 |
| post-filtration | 315 | 7.22 | 44 | 103 | 120 | 0 |

[1]Conjugate = Compound XVIII, para-distearoyl-DTB-mitomycin C
[2]MMC = mitomycin C

B. Cholesterol-Free Liposome Formulation

Liposomes were prepared as described above with a lipid composition of HSPC, mPEG-DSPE and para-distearoyl-DTB-mitomycin C in a molar ratio of 90/5/5. Specifically, 88.5 mg HPSC, 17.9 mg mPEG-DSPE (PEG MW 2000 Daltons) and 7.3 mg of the conjugate were dissolved in 1 mL ethanol. Liposome size, lipid and drug concentration and free mitomycin C concentration in the external suspension medium were determined after each processing step.

| | lipid-DTB-MMC[1,2] Conjugate | lipid | conjugate/ lipid ratio | Liposome Size (nm) | | free MMC[2] |
|---|---|---|---|---|---|---|
| | (μg/mL) | (mg/mL) | | 90° | 30° | (%) |
| post-hydration | 525 | 10.94 | 48 | — | — | 3 |
| post-extrusion | 466 | 9.95 | 47 | 85 | 110 | 6 |
| post-dialysis | 404 | 8.35 | 48 | — | — | 0 |
| post-filtration | 378 | 7.92 | 48 | 82 | 93 | 0 |

[1]Conjugate = Compound XVIII, para-distearoyl-DTB-mitomycin C
[2]MMC = mitomycin C

Example 5

HPLC Conditions for in vitro Characterization

Liposomes prepared as described in Examples 4A–4B were diluted in 0.6 M octaylglucopyranoside. The liposomes were incubated in the presence of 150 mM cysteine at 37° C. Samples with withdrawn at time zero, 30 minutes, 1 hour, 2 hours, 4 hours and 24 hours. A 20 μL volume was analyzed by HPLC using a Water Symmetry C8 3.5×5 cm column.

The flow rate was 1 mL/min and the mobile phase gradient as follows:

| start | 10% MEOH | 90% 10 mM NaPO$_4$, pH = 7 |
|---|---|---|
| 5 min. | 25% MeOH | 75% 10 mM NaPO$_4$, pH = 7 |
| 10 min. | 25% MEOH | 75% 10 mM NaPO$_4$, pH = 7 |
| 15 min. | 100% MeOH | — |
| 25 min. | 100% MeOH | — |
| 30 min. | 10% | 90% 10 mM NaPO$_4$, pH = 7 |
| 35 min. | 10% MEOH | 90% 10 mM NaPO$_4$, pH = 7 |

Example 6

Cytotoxicity Studies

A. Liposome Preparation

Liposomes, prepared as described in Example 4A–4B, were composed of HSPC/mPEG-DSPE/distearoyl-DTB-mitomycin C (90/5/5) or HSPC/cholesterol/mPEG-DSPE,/distearoyl-DTB-mitomycin C (90/45/5/5). The liposome preparations were sterile filtered through 0.45 μm cellulose membranes and were not downsized via extrusion. After liposome formation, mitomycin C concentration was determined by absorbance at 360 nm in liposomes solubilized by 10–20 fold dilution in isopropanol and the phospholipid concentration was determined by inorganic phosphate assay.

The liposomes containing cholesterol had an average diameter of 275±90 nm. The cholesterol-free liposomes had an average diameter of 150±50 nm. The phospholipid concentration in both liposome formulations was 10 μM/mL and the concentration of mitomycin C in both formulations was 120 μg/mL.

B. Chemosensitivity Assay and Growth Rate Determination

The cytotoxic effect of free mitomycin C or mitomycin C in the form of a distearoyl-DTB-mitomycin C conjugate incorporated into liposomes was assayed colorimetrically by a methylene blue staining method described previously (Horowitz, A. T. et al., *Biochim. Biophys. Acta*, 1109:203–209 (1992)) with slight modifications. Upon completion of the assay, the cells were fixed and evaluated using the methylene blue staining assay.

In the assay, 1500 M109 mouse carcinoma cells from exponentially growing cultures in 200 μl aliquots (RPMI-1640 medium+10% fetal bovine serum) were plated onto 96 well flat-bottom microtiter plates. Following 20 hours in culture, during which cells attached and resumed growth, 20 μl of the test formulations (free mitomycin C or liposome formulations) was added to each well. For each 10-fold increase in drug concentration, four drug concentration points were tested. Each test was performed in triplicate wells and in two parallel plates. The cells were treated continuously for 72 hours.

After the 72 hour treatment period, the cultures were fixed by the addition of 50 μl 2.5% glutaraldehyde to each well for 10 minutes. The plates were washed three times with deionized water, once with 0.1 M borate buffer (pH 8.5) and then stained for 60 minutes with 100 μl methylene blue (1% in 0.1 M buffer borate, pH 8.5) at room temperature (20–25° C.). The plates were rinsed in five baths of deionized water to remove non-cell bound dye and then dried. The dye was extracted with 200 μl 0.1 N HCl for 60 minutes at 37° C. and the optical density was determined using a microplate spectrophotometer.

The cell number determined by counting cells with a hemocytometer correlated well with the spectrophotometric absorbance. The initial cell plating density was chosen to ensure a linear relationship between cell number and absorbance at the end of the study. In each study, six wells were fixed before drug was added to determine the initial average absorbance. This value was used to calculate growth rate (GR) and doubling times (DT) of control and drug-treated cells using the following equation: DT=ln 2/ln[(OD$_t$/OD$_c$)/h]; where DT=doubling time in hours; OD$_t$=optical density of test well at the end of the study; OD$_c$=optical density of control well at the start of the study; h=duration of incubation in hours.

The growth rate was calculated as GR=(ln 2/DT). The percent growth inhibition or percent of control growth rate was obtained by dividing the growth rate of drug-treated cells by the growth rate of the untreated, control cells. The drug concentration which caused a 50% inhibition of the control growth rate (IC$_{50}$) was calculated by interpolation of the two closest values of the growth inhibition curve.

Mitomycin C was assayed in the range $10^{-8}$–$10^{-5}$ M. The liposomal formulations with conjugate-bound were assayed in the range $10^{-8}$–$3\times10^{-5}$ M. For interaction studies cysteine (SIGMA, St. Louis, Mo.) was added together with the mitomycin C or liposome formulations to final concentration of 150, 500, or 1000 μM.

The results are shown in Table 1 and in FIGS. 13, 14 and 15A–15B.

Example 7

In vivo Pharmacokinetic Study

A. Liposome Formulations

Liposomes containing cholesterol and cholesterol-free liposomes were prepared as described in Example 5A and 5B.

A solution of mitomycin C in free form was prepared by dissolving 11.9 mg of mitomycin C in 119 μL ethanol. After dissolution, approximately 11.8 μL of a solution of 10 mM histidine/150 mM saline was added. Prior to use, the mitomycin C solution was diluted to 100 μg/mL with the histidine/saline solution and filtered.

B. Animals

Eight rats were randomized into treatment groups as follows:

| Rat No. | Weight (mg) | Formulation | MMC Conc. (mg/mL) | Dose (mL) | Dose (mg/kg) |
|---|---|---|---|---|---|
| 1 | 262.9 | liposomes with chol. | 0.088 | 1.5 | 0.50 |
| 2 | 268.2 | liposomes with chol. | 0.088 | 1.5 | 0.49 |
| 3 | 264.0 | chol-free liposomes | 0.106 | 1.5 | 0.53 |
| 4 | 238.1 | chol-free liposomes | 0.106 | 1.5 | 0.67 |
| 5 | 226.0 | free MMC | 0.1 | 2.26 | 0.66 |
| 6 | 232.0 | free MMC | 0.1 | 2.32 | 0.88 |
| 7 | 250.0 | free MMC | 0.1 | 2.60 | 0.80 |
| 8 | 263.0 | free MMC | 0.1 | 2.63 | 0.59 |

A single intravenous injection of the test formulation was administered as a bolus dose. Blood samples were taken from each animal at the following times after injection: 30 seconds, 15 minutes, 30 minutes, 1 hour, 2 hours, 4 hours, 8 hours, 24 hours, 48 hours, 72 hours and 96 hours. The quantity of mitomycin C in the blood samples was determined by the HPLC procedure given below. A 200 mM iodoacetamine solution was prepared by placing 199.3 mg of iodoacetamide in 5.1 mL of 7.5% EDTA. 15 μL of the 200 mM iodoacetamide solution was placed in each 1 μL of blood sample.

C. HPLC Method for Measuring Mitomycin C in Plasma

1. Solution Preparation

An aqueous buffer containing 10 mM ammonium phosphate, pH=7 was prepared by placing 1.321 g of ammonium phosphate into a 1 L volumetric flask filled with deionized water. The mixture was stirred and the pH was adjusted to 7.0 with o-phosphoric acid. The buffer was filtered through a 0.45 µm nylon filter before use.

A mobile phase of methanol and the aqueous buffer were mixed via a gradient program using a Waters Alliance binary pump.

2. Preparation of Standard Solution and Quality Control Samples

Two separate weights of mitomycin C and mitomycin C conjugate were prepared as standards and quality control samples. One mg of mitomycin C and of mitomycin C conjugate were weighed and dissolved in 1 mL diluent (20% chloroform and 80% methanol mixture) separately. The concentration of the stock solution for both compounds was 1 mg/mL. Several dilutions were made in diluent to obtain concentrations from 5 µg/mL to 100 µg/mL for standard and quality control samples.

An aliquot of 0.1 mL rat plasma was spiked with appropriate volumes (10 µL–50 µL) of mitomycin C and mitomycin C conjugate standard solutions. The concentration ranges were 0.05–5.0 µg/mL and 0.1–5 µg/mL for mitomycin C and mitomycin C conjugate, respectively. The final volume was adjusted to 1 mL with methanol. A similar procedure was followed to prepare quality control samples. The concentrations of quality control samples was 0.1, 0.5 and 5 µg/mL for mitomycin C and 0.1, 1 and 5 µg/mL for mitomycin C conjugate in rat plasma. The samples were spun down at 3,000 rpm for 10 minutes at room temperature. 300 µL of supernatant was transferred to HPLC vials containing 300 µL insert for injection.

3. Sample Preparation

100 µL of plasma sample was denatured with 900 µL of methanol followed by centrifugation for 10 minutes at 3,000 rpm. An aliquot of 300 µL supernatant was transferred to an HPLC vial containing a 300 µL insert for injection.

4. Chromatographic Conditions

A Supelco® C-8, 5 µ, 4.6mm×5 cm column was used. The mobile phase A was 10 mM ammonium phosphate, pH 7. Mobil phase B was methanol. The flow rate was 1 mL/min and detection was by UV at 360 nm. The injection volume was 40 µL and the typical run time was 15 minutes. The gradient program was as follows:

| Time (minutes) | Amount of Mobil Phase A (%) | Amount of Mobil Phase B (%) |
|---|---|---|
| 0 | 90 | 10 |
| 4 | 70 | 30 |
| 8 | 0 | 100 |
| 12 | 90 | 10 |
| 15 | 90 | 10 |

5. Assay and Calculations

The prepared linearity standards (six concentration levels) from low to high concentration were injected. The quality control and plasma samples were then injected for analysis.

Peak area and retention times were determined by the PE-Nelson Turbochrom (Version 4.3) system. Concentrations of mitomycin C and mitomycin C conjugate were calculated using a linear regression program. The linearity of the method was evaluated suing standard responses from six concentration levels. The data were fit to the linear regression dquation y=B*x+A with a weighting factor of $1/x^2$. The precision and accuracy of the method were evaluated from the back-calculated concentrations of the standards as well as from the quality control samples.

The results are shown in FIGS. 16A–16B.

Although the invention has been described with respect to particular embodiments, it will be apparent to those skilled in the art that various changes and modifications can be made without departing from the invention.

What is claimed is:

1. A conjugate for use in a liposomal drug-delivery vehicle, the conjugate having the general structural formula:

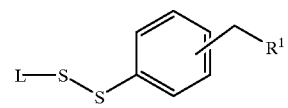

wherein L is a hydrophobic moiety suitable for incorporation into a liposomal lipid bilayer, $R^1$ represents a therapeutic drug covalently attached to the dithiobenzyl moiety, and where orientation of the $CH_2R^1$ group is selected from the ortho position and the para position.

2. The conjugate of claim 1, wherein the therapeutic drug is covalently attached by a linkage selected from the group consisting of urethane, amine, amide, carbonate, thiocarbonate, ether and ester.

3. The conjugate of claim 1, wherein L is selected from the group consisting of cholesterol, a diacylglycerol, and a phospholipid.

4. The conjugate of claim 1, wherein L is a diacylglycerol derivative to yield a conjugate having the general structural formula:

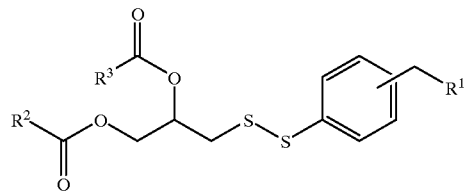

wherein $R^2$ and $R^3$ are hydrocarbons having between about 8 to about 24 carbon atoms.

5. The conjugate of claim 4, wherein $R^2$ and $R^3$ are hydrocarbons having from about 12 to about 22 carbon atoms.

6. The conjugate of claim 4, wherein $R^2$ and $R^3$ are hydrocarbon chains of the same length.

7. The conjugate of claim 1, wherein said drug is selected from the group consisting of mitomycin C, mitomycin A, bleomycin, doxorubicin, daunorubicin, fluorodeoxyuridine, iododeoxyuridine, etoposide, AZT, acyclovir, vidarabine, arabinosyl cytosine, pentostatin, quinidine, atropine, chlorambucil, methotrexate, mitoxantrone and 5-fluorouracil.

8. The conjugate of claim 1, wherein the therapeutic drug is covalently linked to the dithiobenzyl moiety to form a conjugate having the structure:

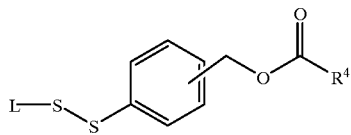

wherein R⁴ represents a residue of the therapeutic drug.

9. The conjugate of claim 8, wherein R⁴ is a therapeutic drug residue containing a primary or a secondary amine moiety thereby forming a urethane linkage between the dithiobenzyl and the therapeutic drug.

10. The conjugate of claim 9, wherein said therapeutic drug is selected from the group consisting of mitomycin A, mitomycin C, bleomycin and a polypeptide.

11. The conjugate of claim 8, wherein R⁴ is a residue of a carboxyl-containing therapeutic drug, thereby to form an ester linkage between the dithiobenzyl and the therapeutic drug.

12. The conjugate of claim 11, wherein said drug is chlorambucil or methotrexate.

13. The conjugate of claim 8, wherein R⁴ is a therapeutic drug residue containing a hydroxyl moiety thereby to form a carbonate linkage between the dithiobenzyl and the therapeutic drug.

14. The conjugate of claim 13, wherein the therapeutic drug is selected from the group consisting of fluorodeoxyuridine, iododeoxyuridine, etoposide, AZT, acyclovir, vidarabine, arabinosyl cytosine, pentostatin, quinidine, mitoxantrone and atropine.

15. A liposome composition, comprising liposomes comprised of vesicle-forming lipids including from about 1 to about 30 mole percent of a conjugate having the general structural formula:

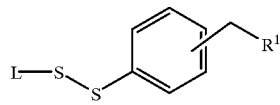

wherein L is a hydrophobic moiety suitable for incorporation into a liposomal lipid bilayer, R¹ represents a therapeutic drug covalently attached to the dithiobenzyl moiety, and where orientation of the CH₂R¹ group is selected from the ortho position and the para position, wherein said therapeutic drug is released from the conjugate in vivo in response to a physiologic condition or an artificially induced condition.

16. The conjugate of claim 15, wherein the therapeutic drug is covalently attached to the dithiobenzyl moiety by a linkage selected from the group consisting of urethane, amine; amide, carbonate, thio-carbonate, ether and ester.

17. The conjugate of claim 1, wherein L is selected from the group consisting of cholesterol, a diacylglycerol, and a phospholipid.

18. The conjugate of claim 15, wherein L is a diacylglycerol to yield a conjugate having the structural formula:

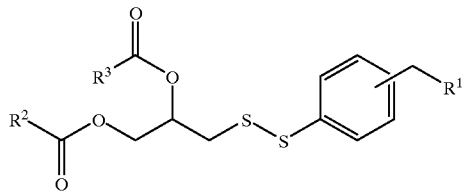

wherein R² and R³ are hydrocarbons having between about 8 to about 24 carbon atoms.

19. The conjugate of claim 18, wherein R² and R³ are hydrocarbons having from about 12 to about 22 carbon atoms.

20. The conjugate of claim 18, wherein R² and R³ are hydrocarbon chains of the same length.

21. The conjugate of claim 15, wherein said drug is selected from the group consisting of mitomycin C, mitomycin A, bleomycin, doxorubicin, daunorubicin, fluorodeoxyuridine, iododeoxyuridine, etoposide, AZT, acyclovir, vidarabine, arabinosyl cytosine, pentostatin, quinidine, atropine, chlorambucil, methotrexate, mitoxantrone and 5-fluorouracil.

22. The conjugate of claim 15, wherein the therapeutic drug is covalently linked to the dithiobenzyl moiety to form a conjugate having the structure:

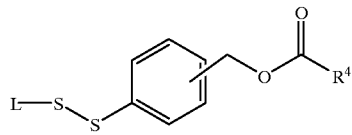

wherein R⁴ represents a residue of the therapeutic drug.

23. The conjugate of claim 22, wherein R⁴ is a therapeutic drug residue containing a primary or a secondary amine moiety thereby forming a urethane linkage between the dithiobenzyl and the therapeutic drug.

24. The conjugate of claim 23, wherein said therapeutic drug is selected from the group consisting of mitomycin A, mitomycin C, bleomycin and a polypeptide.

25. The conjugate of claim 22, wherein R⁴ is a residue of a carboxyl-containing therapeutic drug, thereby to form an ester linkage between the dithiobenzyl and the therapeutic drug.

26. The conjugate of claim 25, wherein said drug is chlorambucil or methotrexate.

27. The conjugate of claim 22, wherein R⁴ is a therapeutic drug residue containing a hydroxyl moiety thereby to form a carbonate linkage between the dithiobenzyl and the therapeutic drug.

28. The conjugate of claim 27, wherein the therapeutic drug is selected from the group consisting of fluorodeoxyuridine, iododeoxyuridine, etoposide, AZT, acyclovir, vidarabine, arabinosyl cytosine, pentostatin, quinidine, mitoxantrone and atropine.

29. A method for retaining a drug in a liposome, comprising preparing liposomes comprised of a vesicle-forming lipid and of between about 1 to about 30 mole percent of a conjugate having the general form:

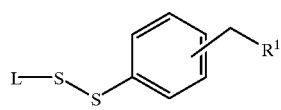

wherein L is a hydrophobic moiety suitable for incorporation into a liposomal lipid bilayer, $R^1$ represents a therapeutic drug covalently attached to the dithiobenzyl moiety, and where orientation of the $CH_2R^1$ group is selected from the ortho position and the para position, whereby said preparing is effective to retain the drug in the liposomes until release from the conjugate in response to a physiologic condition or an artificially induced condition.

30. The method of claim 29, wherein said preparing includes preparing a conjugate where the therapeutic drug is covalently attached by a linkage selected from the group consisting of urethane, amine, amide, carbonate, thiocarbonate, ether and ester.

31. The conjugate of claim 1, wherein L is selected from the group consisting of cholesterol, a diacylglycerol, and a phospholipid.

32. The method of claim 29, wherein said preparing includes preparing a conjugate wherein L is a diacylglycerol to yield a conjugate having the general structural formula:

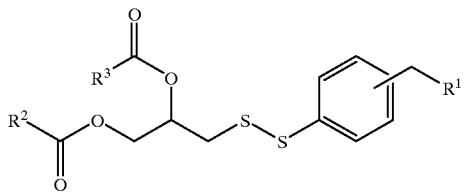

wherein $R^2$ and $R^3$ are hydrocarbons having between about 8 to about 24 carbon atoms.

33. The method of claim 18, wherein $R^2$ and $R^3$ are hydrocarbons having from about 12 to about 22 carbon atoms.

34. The conjugate of claim 32, wherein $R^2$ and $R^3$ are hydrocarbon chains of the same length.

35. The method of claim 29, wherein said preparing includes preparing a conjugate comprising a drug selected from the group consisting of mitomycin C, mitomycin A, bleomycin, doxorubicin, daunorubicin, fluorodeoxyuridine, iododeoxyuridine, etoposide, AZT, acyclovir, vidarabine, arabinosyl cytosine, pentostatin, quinidine, atropine, chlorambucil, methotrexate, mitoxantrone and 5-fluorouracil.

36. The method of claim 29, wherein said preparing includes preparing a conjugate comprising a therapeutic drug covalently linked to the dithiobenzyl moiety to form a conjugate having the structure:

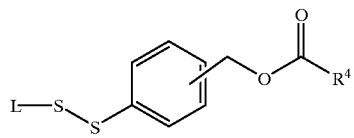

wherein $R^4$ represents a residue of the therapeutic drug.

37. The method of claim 36, wherein $R^4$ is a therapeutic drug residue containing a primary or a secondary amine moiety thereby forming a urethane linkage between the dithiobenzyl and the therapeutic drug.

38. The method of claim 37, wherein said therapeutic drug is selected from the group consisting of mitomycin A, mitomycin C, bleomycin and a polypeptide.

39. The method of claim 36, wherein $R^4$ is a residue of a carboxyl-containing therapeutic drug, thereby to form an ester linkage between the dithiobenzyl and the therapeutic drug.

40. The method of claim 39, wherein said drug is chlorambucil or methotrexate.

41. The method of claim 36, wherein $R^4$ is a therapeutic drug residue containing a hydroxyl moiety thereby to form a carbonate linkage between the dithiobenzyl and the therapeutic drug.

42. The method of claim 41, wherein the therapeutic drug is selected from the group consisting of fluorodeoxyuridine, iododeoxyuridine, etoposide, AZT, acyclovir, vidarabine, arabinosyl cytosine, pentostatin, quinidine, mitoxantrone and atropine.

* * * * *

US006365179C1

(12) EX PARTE REEXAMINATION CERTIFICATE (4907th)
United States Patent
Zalipsky et al.

(10) Number: US 6,365,179 C1
(45) Certificate Issued: Feb. 10, 2004

(54) CONJUGATE HAVING A CLEAVABLE LINKAGE FOR USE IN A LIPOSOME

(75) Inventors: Samuel Zalipsky, Redwood City, CA (US); Alberto A. Gabizon, Jerusalem (IL)

(73) Assignee: Hadasit Medical Research Services and Development Ltd., Jerusalem (IL)

Reexamination Request:
No. 90/006,556, Feb. 24, 2003

Reexamination Certificate for:
Patent No.: 6,365,179
Issued: Apr. 2, 2002
Appl. No.: 09/556,610
Filed: Apr. 21, 2000

Related U.S. Application Data
(60) Provisional application No. 60/130,897, filed on Apr. 23, 1999.

(51) Int. Cl.[7] .................. A61K 9/127; A61K 38/00; C08D 11/00; A01N 61/00
(52) U.S. Cl. ............. 424/450; 424/85.1; 205/254; 530/336; 536/84; 514/1
(58) Field of Search .................. 424/450, 85.1; 205/254; 530/336; 536/84; 514/1

(56) References Cited

FOREIGN PATENT DOCUMENTS

EP          0 317 957 A2     5/1989

OTHER PUBLICATIONS

Senter, P.D., et al., *J. Org Chem* 55(9):2975–2978, (1990).

*Primary Examiner*—Kenneth R. Horlick

(57) ABSTRACT

Conjugates of a hydrophobic moiety, such as a lipid, linked through a cleavable dithiobenzyl linkage to a therapeutic agent are described. The dithiobenzyl linkage is susceptible to cleavage by mild thiolysis, resulting in release of the therapeutic agent in its original form. The linkage is stable under nonreducing conditions. The conjugate can be incorporated into liposomes for administration in vivo and release of the therapeutic agent in response to endogenous in vivo reducing conditions or in response to administration of an exogenous reducing agent.

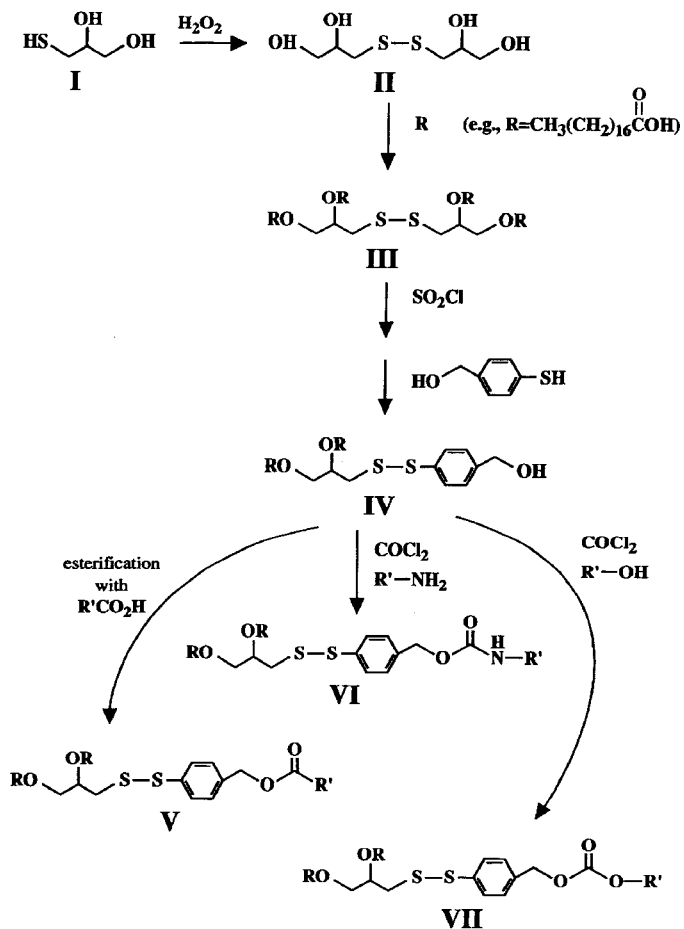

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–30, 32, and 34–42 is confirmed.

Claims 31 and 33 are determined to be patentable as amended.

31. The [conjugate] *method* of claim [1] *29*, wherein *said preparing includes preparing a conjugate wherein* L is selected from the group consisting of cholesterol, a diacylglycerol, and a phospholipid.

33. The method of claim [29] *32*, wherein $R^2$ and $R^3$ are hydrocarbons having from about 12 to about 22 carbon atoms.

* * * * *